(12) United States Patent
Bakker et al.

(10) Patent No.: US 6,953,843 B2
(45) Date of Patent: Oct. 11, 2005

(54) ANTIBODIES AND FRAGMENTS THEREOF TO MDL-1 PROTEIN

(75) Inventors: Alexander B. H. Bakker, San Francisco, CA (US); Joseph H. Phillips, Palo Alto, CA (US); Lewis L. Lanier, Los Altos, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/191,732

(22) Filed: Jul. 8, 2002

(65) Prior Publication Data

US 2005/0084900 A1 Apr. 21, 2005

Related U.S. Application Data

(62) Division of application No. 09/127,946, filed on Jul. 31, 1998, now Pat. No. 6,416,973.
(60) Provisional application No. 60/089,168, filed on Jun. 12, 1998, provisional application No. 60/069,639, filed on Dec. 15, 1997, provisional application No. 60/063,717, filed on Oct. 29, 1997, provisional application No. 60/069,692, filed on Dec. 16, 1997, and provisional application No. 60/054,430, filed on Aug. 1, 1997.

(51) Int. Cl.[7] .............................................. C07K 16/28
(52) U.S. Cl. ................. 530/391.3; 530/350; 530/387.9; 530/388.1; 530/388.22; 530/387.3; 530/389.1; 424/133.1; 424/135.1; 424/139.1; 424/143.1; 424/144.1
(58) Field of Search .............................. 530/350, 389.1, 530/388.22, 387.3; 424/1.37, 133.1, 139.1, 144.1; 514/2

(56) References Cited

U.S. PATENT DOCUMENTS

2003/0022279 A1 * 1/2003 Fraser et al. ................ 435/69.1

FOREIGN PATENT DOCUMENTS

| WO | WO 94/01548 | 1/1994 |
|---|---|---|
| WO | WO 96/26961 | 9/1996 |
| WO | WO 97/20046 | 6/1997 |
| WO | WO 98/39446 | 9/1998 |
| WO | WO 98/49292 | 11/1998 |
| WO | WO 99/06548 | 2/1999 |
| WO | WO 99/06554 | 2/1999 |

OTHER PUBLICATIONS

José Aramburu, et al., *The Journal of Immunology*, 144(8):3238–3247, Apr.15, 1990 "A novel functional cell surface dimer (Kp43) expressed by natural killer cells and T cell receptor–γ/δ TCR+ T lymphocytes I. Inhibition of the IL–2–Dependent Proliferation by Anti–Kp43 Monoclonal Antibody".

José Aramburu, et al., *The Journal of Immunology*, 147(2):714–721, Jul. 15, 1991 "A novel functional cell surface dimer (Kp43) expressed by natural killer cells and T cell receptor–γ/δ TCR+ T lymphocytes II. Modulation of Natural Killer Cytotoxicity by Anti–Kp43 Monoclonal Antibody".

A. Bernot, et al., *GenBank*, Accession No. M88072, Jun. 24, 1994. Definition: "Gallus gallus (17.5) mRNA, complete cds.".

Mathieu Bléry, et al., *J. Biol. Chem.*, 272(14):8989–8996, Apr. 4, 1997. "Reconstiuted Killer Cell Inhibitory Receptors for Major Histocompatibility Complex Class I Molecules Control Mast Cell Activation Induced via Immunoreceptor Tyrosine–based Activation Motifs".

John C. Cambier, *Immunology Today*, 16(2):110, 1995. "New nomenclature for the Reth motif (or ARH1/TAM/ARAM/YXXL)".

John C. Cambier, et al., *Proc. Natl. Acad. Sci. USA*, 94:5993–5995, Jun. 1997. "Inhibitory receptors abound?".

Marco Colonna, *NATURE*, 391:642–643, Feb. 12, 1998. "Unmasking the killer's accomplice".

Marco Colonna and Jacqueline Samaridis, *SCIENCE*, 268:405–408, Apr. 21, 1995. "Cloning of Immunoglobulin–Superfamily Members Associated with HLA–C and HLA–B Recognition by Human Natural Killer Cells".

Marc Daëron, et al., *Immunity*, 3:635–646, Nov. 1995. "The Same Tyrosine–Based Inhibition Motif, in the Intracytoplasmic Domain of FCγRIIB, Regulates Negatively BCR–, TCR–, and FcR–Dependent Cell Activation".

A. D'Andrea, et al., *The Journal of Immunology*, 155:2306–2310, 1995. "Molecular Cloning of NKB1, a Natural Killer Cell Receptor for HLA–B Allotypes".

R. Giorda, et al., *GenBank*, Accession No. M62891, Sep. 14, 1992. Definition: "R.norvegicus 3.2.3 antigen protein mRNA, complete cds.".

J. Hamann, et al., *GenBank*, Accession No. L07555, Apr. 21, 1997. Definition: "*Homo sapiens* early activation antigen CD69 mRNA, complete cds.".

L. Hillier, et al., *GenBank*, Accession No. AA412675, May 2, 1997. Definition: "zu12c03.s1 Soares_testis_NHT *Homo sapiens* cDNA clone IMAGE:731620 3', MRNA sequence".

L. Hillier, et al., *GenBank*, Accession No. AA480109, Aug. 8, 1997. Definition: "zv41f05.s1 Soares ovary tumor NbHOT *Homo sapiens* cDNA clone 756225 3' similar to TR:G498729 G498729 Zinc Finger Protein".

(Continued)

Primary Examiner—Lorraine Spector
Assistant Examiner—Eileen B. O'Hara
(74) Attorney, Agent, or Firm—Edwin P. Ching; Sheela Mohan-Peterson

(57) ABSTRACT

The purification and isolation of various genes which encode mammalian cell surface polypeptides. Nucleic acids, proteins, antibodies, and other reagents useful in modulating development of cells, e.g., lymphoid and myeloid, are provided, along with methods for their use.

4 Claims, No Drawings

OTHER PUBLICATIONS

L. Hillier, et al., *GenBank*, Accession No. AA481924, Aug. 8, 1997. Definition: "zv41f05.r1 Soares ovary tumor NbHOT *Homo sapiens* cDNA clone 756225 5' similar to TR:G498729 G498729 Zinc Finger Protein".

L. Hillier, et al., *GenBank*, Accession No. H12338, Jun. 27, 1995. Definition: "yj11h03s1 *Homo sapiens* cDNA clone 148469 3'.".

L. Hillier, et al., *GenBank*, Accession No. H12392, Jun. 27, 1995. Definition: "yj11h03.r1 *Homo sapiens* cDNA clone 148469 5'.".

L. Hillier, et al., *GenBank*, Accession No. H39980, Aug. 16, 1995. Definition: "yjo55g07.r1 *Homo sapiens* cDNA clone 181884 5'.".

L. Hillier, et al., *GenBank*, Accession No. N41026, Jan. 22, 1996. Definition: "yy53c02.s1 *Homo sapiens* cDNA clone 277250 3' similar to PIR:S47066 S47066 zinc finger protein –human.".

L. Hillier, et al., *GenBank*, Accession No. R49793, May 18, 1995. Definition: "yj55f08.r1 *Homo sapiens* cDNA clone 152679 5'.".

L. Hillier, et al., *GenBank*, Accession No. T52100, Feb., 8, 1995. Definition: "yb10h09.r1 *Homo sapiens* cDNA clone 70817 5'.".

L. Hillier, et al., *GenBank*, Accession No. 55959, Feb. 8, 1995. Definition: "yb35f06.r1 *Homo sapiens* cDNA clone 73187 5'.".

L. Hillier, et al., *GenBank*, Accession No. W60864, Oct. 15, 1996. Definition: "zd27g05.s1 Soares fetal heart NbHH19W *Homo sapiens* cDNA clone 341912 3' similar to PIR:S47066 S47066 zinc finger protein—human".

L. Hillier, et al., *GenBank*, Accession No. W60940, Oct. 15, 1996. Definition: "27g05.r1 Soares fetal heart NbHH19W *Homo sapiens* cDNA clone 341912 5'.".

L. Hillier, et al., *GenBank*, Accession No. W74783, Oct. 16, 1996. Definition: "zd57c01.r1 Soares fetal heart NbHH19W *Homo sapiens* cDNA clone 344736 5'.".

L. Hillier, et al., *GenBank*, Accession No. W92376, Jul. 16, 1996. Definition: "zd99g11.s1 Soares fetal heart NbHH19W *Homo sapiens* cDNA clone 357668 3" similar to PIR:S47066 S47066 zinc finger protein—human".

Lewis L. Lanier, et al., *Immunity*, 8:693–701, Jun. 1998. "Association of DAP12 with Activating CD94/NKG2C NK Cell Receptors".

Lewis L. Lanier, et al., *Nature*, 391:703–707, Feb. 12, 1998. "Immunoreceptor DAP12 bearing a tyrosine–based activation motif is involved in activating NK cells".

Lewis L. Lanier, *Immunity*, 6:371–378, Apr. 1997. "Natural Killer Cells: From No Receptors to Too Many".

Paul J. Leibson, Immunity, 3:5–8, Jul. 1995. "MHC–Recognizing Receptors: They're Not Just for T Cells Anymore".

Bernard Malissen, *NATURE*, 384:518–519, Dec. 12, 1996. "Two faces are better than one".

M. Marra, et al., *GenBank*, Accession No. AA098506, Oct. 25,, 1996. Definition: "mo08f09.r1 Life Tech mouse embryo 10 5dpc 10665016 *Mus musculus* cDNA clone 553001 5'.".

M. Marra, et al., *GenBank*, Accession No. AA186015, Feb. 17, 1997. Definition: mt35c02.r1 Soares mouse 3NbMS *Mus musculus* cDNA clone IMAGE:623042 5' similar to SW:NK13_RAT P27471 Natural Killer Cell Surface Protein P1–3.2.3;, mRNA sequence.

M. Marra, et al., *GenBank*, Accession No. AA242315, Mar. 7, 1997. Definition: "mw26h05.r1 Soares mouse 3NMW12 5 *Mus musculus* cDNA clone 671865 5'.".

M. Marra, et al., *GenBank*, Accession No. AA138406, Feb. 16, 1997. Definition: "mr12f09.r1 Soares mouse 3NbMS *Mus musculus* cDNA clone 597257 5'.".

M. Marra, et al., *GenBank*, Accession No. W41142, Sep. 11, 1996. Definition: "mc38h03.r1 Soares mouse p3NMF19.5 *Mus musculus* cDNA clone 350837 5'.".

M. Marra, et al., *GenBank*, Accession No. W88159, Sep. 12, 1996. Definition: "mf69f10.r1 Soares mouse embryo NbME13.5 14.5 *Mus musculus* cDNA clone 419563 5'.".

M. Marra, et al., *GenBank*, Accession No. W91184, Sep. 12, 1996. Definition: "mf72b05.r1 Soares mouse embryo 3NbME13.5 14.5 *Mus musculus* cDNA clone 419793 5'.".

M. Marra, et al., *GenBank*, Accession No. W13188, Oct. 2, 1997. Definition: mb31f12.r1 Soares mouse p3NMF19.5 *Mus musculus* cDNA clone IMAGE:331055 5', mRNA sequence.

Alessandro Moretta, et al., *Annual Review of Immunology*, 14:619–648, 1996. "Receptors for HLA Class–I Molecules in Human Natural Killer Cells".

NCI–CGAP (Robert Strausberg), *GenBank*, Accession No. AA516481, Jan. 5, 1998. Definition: nh52a05.r1 NCI_CGAP_Pr5 *Homo sapiens* cDNA clone IMAGE:955952, mRNA sequence.

Lucia Olcese, et al., *The Journal of Immunology*, 158:5083–5086, 1997. "Human Killer Cell Activatory Receptors for MHC Class I Molecules Are Included in a Multimeric Complex Expressed by Natural Killer Cells".

Gonzalo Rubio, et al., *The Journal of Immunology*, 151(3):1312–1321, Aug. 1, 1993. "A Novel Functional Cell Surface Dimer (kp43) Serves as Accessory Molecule for the Activation of a Subset of Human γδ T Cells".

Jacqueline Samardis and Marco Colonna, *Eur. J. Immunology*, 27:660–665, 1997. "Cloning of novel immunoglobulin superfamily receptors expressed on human myeloid and lymphoid cells: structural evidence for new stimulatory and inhibitory pathways".

Andrew M. Scharenberg and Jean–Pierre Kinet, *Cell*, 87:961–964, Dec. 13, 1996. "The Emerging Field of Receptor–Mediated Inhibitory Signaling: SHP or SHIP?".

Kathleen M. Smith, et al., *The Journal of Immunology*, 161(1):7–10, Jul. 1, 1998. "Cutting Edge: Ly–49D and Ly–49H Associate with Mouse DAP12 and Form Activating Receptors".

Kan Takase, et al., *The Journal of Immunology*, 159:741–747, 1997. A New 12–Kilodalton Dimer Associated with Pre–TCR Complex and Clonotype–Independent CD3 Complex on Immature Thymocytes.

Matthew L. Thomas, *Journal of Experimental Medicine*, 181:1953–1956, Jun. 1995. "Of ITAMs and ITIMs: Turning On and Off the B Cell Antigen Receptor".

Nicolai Wagtmann, et al., *Immunity*, 2:439–449, 1995. "Molecular Clones of the p58 NK Cell Receptor Reveal Immunoglobulin–Related Molecules with Diversity in Both the Extra– and Intracellular Domains".

* cited by examiner

SEQUENCE LISTING (1) GENERAL INFORMATION:

(iii) NUMBER OF SEQUENCES: 14

(2) INFORMATION FOR SEQ ID NO: 1:

```
    (i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..339

(ix) FEATURE:
        (A) NAME/KEY: mat_peptide
        (B) LOCATION: 79..339

(xi) SEQUENCE DESCRIPTION: SEQ ID NO: 1:
```

| | | | | | | | | | | | | | | | | |
|---|---|---|---|---|---|---|---|---|---|---|---|---|---|---|---|---|
| ATG | GGG | GGA | CTT | GAA | CCC | TGC | AGC | AGG | CTC | CTG | CTC | CTG | CCT | CTC | CTG | 48 |
| Met | Gly | Gly | Leu | Glu | Pro | Cys | Ser | Arg | Leu | Leu | Leu | Leu | Pro | Leu | Leu | |
| -26 | -25 | | | | -20 | | | | | -15 | | | | | | |

```
CTG GCT GTA AGT GGT CTC CGT CCT GTC CAG GCC CAG GCC CAG AGC GAT        96
Leu Ala Val Ser Gly Leu Arg Pro Val Gln Ala Gln Ala Gln Ser Asp
-10              -5                   1               5

TGC AGT TGC TCT ACG GTG AGC CCG GGC GTG CTG GCA GGG ATC GTG ATG       144
Cys Ser Cys Ser Thr Val Ser Pro Gly Val Leu Ala Gly Ile Val Met
             10                  15                  20

GGA GAC CTG GTG CTG ACA GTG CTC ATT GCC CTG GCC GTG TAC TTC CTG       192
Gly Asp Leu Val Leu Thr Val Leu Ile Ala Leu Ala Val Tyr Phe Leu
         25                  30                  35

GGC CGG CTG GTC CCT CGG GGG CGA GGG GCT GCG GAG GCA GCG ACC CGG       240
Gly Arg Leu Val Pro Arg Gly Arg Gly Ala Ala Glu Ala Ala Thr Arg
 40                  45                  50

AAA CAG CGT ATC ACT GAG ACC GAG TCG CCT TAT CAG GAG CTC CAG GGT       288
Lys Gln Arg Ile Thr Glu Thr Glu Ser Pro Tyr Gln Glu Leu Gln Gly
 55                  60                  65                  70

CAG AGG TCG GAT GTC TAC AGC GAC CTC AAC ACA CAG AGG CCG TAT TAC       336
Gln Arg Ser Asp Val Tyr Ser Asp Leu Asn Thr Gln Arg Pro Tyr Tyr
             75                  80                  85

AAA TGA                                                                342
Lys (2) INFORMATION FOR SEQ ID NO: 2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Gly Leu Glu Pro Cys Ser Arg Leu Leu Leu Leu Pro Leu Leu
-26 -25              -20                  -15

Leu Ala Val Ser Gly Leu Arg Pro Val Gln Ala Gln Ala Gln Ser Asp
-10              -5                   1               5

Cys Ser Cys Ser Thr Val Ser Pro Gly Val Leu Ala Gly Ile Val Met
             10                  15                  20

Gly Asp Leu Val Leu Thr Val Leu Ile Ala Leu Ala Val Tyr Phe Leu
         25                  30                  35

Gly Arg Leu Val Pro Arg Gly Arg Gly Ala Ala Glu Ala Ala Thr Arg
 40                  45                  50

Lys Gln Arg Ile Thr Glu Thr Glu Ser Pro Tyr Gln Glu Leu Gln Gly
 55                  60                  65                  70
```

Gln Arg Ser Asp Val Tyr Ser Asp Leu Asn Thr Gln Arg Pro Tyr Tyr
            75                  80                  85

Lys (2) INFORMATION FOR SEQ ID NO: 3:

(i) SEQUENCE CHARACTERISTICS:
        (A) LENGTH: 628 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CTTGCCTGGA CGCTGCGCCA CATCCCACCG GCCCTTACAC TGTGGTGTCC AGCAGCATCC      60

GGCTTCATGG GGGGACTTGA ACCCTGCAGC AGGCTCCTGC TCCTGCCTCT CCTGCTGGCT     120

GTAAGTGGTC TCCGTCCTGT CCAGGCCCAG GCCCAGAGCG ATTGCAGTTG CTCTACGGTG     180

AGCCCGGGCG TGCTGGCAGG GATCGTGATG GGAGACCTGG TGCTGACAGT GCTCATTGCC     240

CTGGCCGTGT ACTTCCTGGG CCGGCTGGTC CCTCGGGGGC GAGGGGCTGC GGAGGCAGCG     300

ACCCGGAAAC AGCGTATCAC TGAGACCGAG TCGCCTTATC AGGAGCTCCA GGGTCAGAGG     360

TCGGATGTCT ACAGCGACCT CAACACACAG AGGCCGTATT ACAAATGAGC CCGAATCATG     420

ACAGTCAGCA ACATGATACC TGGATCCAGC CATTCCTGAA GCCCANCCTG CACCTCATTC     480

CAACTCCTAC CGCGATACAG ACCCACAGAG TGCCATCCCT GAGAGACCAG ACCGCTCCCC     540

AATACTCTCC TAAATAAAC ATGAAGCACA AAAAAAAAA AAAAAAAAC TCNGGGGGG       600

GGCCCGGTTA NCCAATTTGG NCCTAAAG                                        628
```

(2) INFORMATION FOR SEQ ID NO: 4:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO: 4:

Glu Ser Pro Tyr Gln Glu Leu Gln Gly Gln Arg Ser Asp Val Tyr Ser
1               5                   10                  15

Asp Leu (2) INFORMATION FOR SEQ ID NO: 5:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..342

(ix) FEATURE:
        (A) NAME/KEY: mat_peptide
        (B) LOCATION: 79..342

(xi) SEQUENCE DESCRIPTION: SEQ ID NO: 5:

```
ATG GGG GCT CTG GAG CCC TCC TGG TGC CTT CTG TTC CTT CCT GTC CTC        48
Met Gly Ala Leu Glu Pro Ser Trp Cys Leu Leu Phe Leu Pro Val Leu
-26 -25                 -20                 -15

CTG ACT GTG GGA GGA TTA AGT CCC GTA CAG GCC CAG AGT GAC ACT TTC        96
Leu Thr Val Gly Gly Leu Ser Pro Val Gln Ala Gln Ser Asp Thr Phe
-10                 -5                  1                   5

CCA AGA TGC GAC TGT TCT TCC GTG AGC CCT GGT GTA CTG GCT GGG ATT       144
Pro Arg Cys Asp Cys Ser Ser Val Ser Pro Gly Val Leu Ala Gly Ile
                10                  15                  20

GTT CTG GGT GAC TTG GTG TTG ACT CTG CTG ATT GCC CTG GCT GTG TAC       192
Val Leu Gly Asp Leu Val Leu Thr Leu Leu Ile Ala Leu Ala Val Tyr
            25                  30                  35

TCT CTG GGC CGC CTG GTC TCC CGA GGT CAA GGG ACA GCG GAA GGG ACC       240
Ser Leu Gly Arg Leu Val Ser Arg Gly Gln Gly Thr Ala Glu Gly Thr
        40                  45                  50

CGG AAA CAA CAC ATT GCT GAG ACT GAG TCG CCT TAT CAG GAG CTT CAG       288
Arg Lys Gln His Ile Ala Glu Thr Glu Ser Pro Tyr Gln Glu Leu Gln
55                  60                  65                  70

GGT CAG AGA CCA GAA GTA TAC AGT GAC CTC AAC ACA CAG AGG CAA TAT       336
Gly Gln Arg Pro Glu Val Tyr Ser Asp Leu Asn Thr Gln Arg Gln Tyr
                75                  80                  85

TAC AGA TGA                                                           345
Tyr Arg
```

(2) INFORMATION FOR SEQ ID NO: 6:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Gly Ala Leu Glu Pro Ser Trp Cys Leu Leu Phe Leu Pro Val Leu
-26 -25                 -20                 -15

Leu Thr Val Gly Gly Leu Ser Pro Val Gln Ala Gln Ser Asp Thr Phe
-10                 -5                  1                   5

Pro Arg Cys Asp Cys Ser Ser Val Ser Pro Gly Val Leu Ala Gly Ile
                10                  15                  20

Val Leu Gly Asp Leu Val Leu Thr Leu Leu Ile Ala Leu Ala Val Tyr
            25                  30                  35

Ser Leu Gly Arg Leu Val Ser Arg Gly Gln Gly Thr Ala Glu Gly Thr
        40                  45                  50

Arg Lys Gln His Ile Ala Glu Thr Glu Ser Pro Tyr Gln Glu Leu Gln
55                  60                  65                  70

Gly Gln Arg Pro Glu Val Tyr Ser Asp Leu Asn Thr Gln Arg Gln Tyr
                75                  80                  85

Tyr Arg
```

(2) INFORMATION FOR SEQ ID NO: 7:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 63..338

(ix) FEATURE:
        (A) NAME/KEY: mat_peptide
        (B) LOCATION: 117..338

(xi) SEQUENCE DESCRIPTION: SEQ ID NO: 7:

```
GTCGACCTGG ACTTCTCTGG ACCACAGTCC TCTGCCAGAC CCCTGCCAGA CCCCAGTCCA        60

CC ATG ATC CAT CTG GGT CAC ATC CTC TTC CTG CTT TTG CTC CCA GTG          107
   Met Ile His Leu Gly His Ile Leu Phe Leu Leu Leu Leu Pro Val
   -18         -15                 -10                 -5

GCT GCA GCT CAG ACG ACT CCA GGA GAG AGA TCA TCA CTC CCT GCC TTT         155
Ala Ala Ala Gln Thr Thr Pro Gly Glu Arg Ser Ser Leu Pro Ala Phe
            1               5                   10

TAC CCT GGC ACT TCA GGC TCT TGT TCC GGA TGT GGG TCC CTC TCT CTG         203
Tyr Pro Gly Thr Ser Gly Ser Cys Ser Gly Cys Gly Ser Leu Ser Leu
        15              20                  25

CCG CTC CTG GCA GGC CTC GTG GCT GCT GAT GCG GTG GCA TCG CTG CTC         251
Pro Leu Leu Ala Gly Leu Val Ala Ala Asp Ala Val Ala Ser Leu Leu
30              35                  40                      45

ATC GTG GGG GCG GTG TTC CTG TGC GCA CGC CCA CGC CGC AGC CCC GCC         299
Ile Val Gly Ala Val Phe Leu Cys Ala Arg Pro Arg Arg Ser Pro Ala
                50                  55                  60

CAA GAT GGC AAA GTC TAC ATC AAC ATG CCA GGC AGG GGC TGACCCTCCT          348
Gln Asp Gly Lys Val Tyr Ile Asn Met Pro Gly Arg Gly
                65                  70

GCAGCTTGGA CCTTTGACTT CTGACCCTCT CATCCTGGAT GGTGTGTGGT GCACAGGAAA       408

CCCCGCCCCA ACTTTTGGAT TGTAATAAAA CATTTGAAAC ACA                         451
```

(2) INFORMATION FOR SEQ ID NO: 8:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ile His Leu Gly His Ile Leu Phe Leu Leu Leu Leu Pro Val Ala
-18         -15                 -10                 -5

Ala Ala Gln Thr Thr Pro Gly Glu Arg Ser Ser Leu Pro Ala Phe Tyr
        1               5                   10

Pro Gly Thr Ser Gly Ser Cys Ser Gly Cys Gly Ser Leu Ser Leu Pro
15              20                  25                      30

Leu Leu Ala Gly Leu Val Ala Ala Asp Ala Val Ala Ser Leu Leu Ile
                35                  40                  45

Val Gly Ala Val Phe Leu Cys Ala Arg Pro Arg Arg Ser Pro Ala Gln
            50                  55                  60

Asp Gly Lys Val Tyr Ile Asn Met Pro Gly Arg Gly
            65                  70
```

(2) INFORMATION FOR SEQ ID NO: 9:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (ii) MOLECULE TYPE: cDNA (ix) FEATURE:
              (A) NAME/KEY: CDS
              (B) LOCATION: 109..345

(ix) FEATURE:
              (A) NAME/KEY: mat_peptide
              (B) LOCATION: 163..345

(xi) SEQUENCE DESCRIPTION: SEQ ID NO: 9:

GTCACCATCG GGGTGACATC CGTCCTAGCT GCCTCTCTTC TCCTCTACTG TTCTGAGGAC         60

TTCCCTGGAC CACAGTTTTG GCCAGATCCC TTCAGGTCCC AGCCCAGC ATG GAC CCC        117
                                                     Met Asp Pro
                                                     -18

CCA GGC TAC CTC CTG TTC CTG CTT CTG CTC CCA GTG GCT GCA AGT CAG        165
Pro Gly Tyr Leu Leu Phe Leu Leu Leu Leu Pro Val Ala Ala Ser Gln
-15             -10                 -5                           1

ACA TCG GCA GGT TCC TGC TCC GGA TGT GGG ACT CTG TCT CTG CCA CTC        213
Thr Ser Ala Gly Ser Cys Ser Gly Cys Gly Thr Leu Ser Leu Pro Leu
                5                   10                  15

CTG GCA GGC CTA GTG GCT GCA GAT GCG GTC ATG TCA CTC CTA ATT GTA        261
Leu Ala Gly Leu Val Ala Ala Asp Ala Val Met Ser Leu Leu Ile Val
        20                  25                  30

GGG GTG GTG TTT GTA TGT ATG CGC CCA CAC GGC AGG CCT GCC CAA GAA        309
Gly Val Val Phe Val Cys Met Arg Pro His Gly Arg Pro Ala Gln Glu
        35                  40                  45

GAT GGT AGA GTC TAC ATC AAC ATG CCT GGC AGA GGC TGACCACGGC             355
Asp Gly Arg Val Tyr Ile Asn Met Pro Gly Arg Gly
50                  55                  60

ACCTTCTGAC CCGCTCATCC TGGATCCTGT GGGTTTGGGG TGCGTGGG                   403

(2) INFORMATION FOR SEQ ID NO: 10:

(i) SEQUENCE CHARACTERISTICS:
              (A) LENGTH: 79 amino acids
              (B) TYPE: amino acid
              (D) TOPOLOGY: linear (ii) MOLECULE TYPE: protein (xi) SEQUENCE DESCRIPTION: SEQ ID NO: 10:

Met Asp Pro Pro Gly Tyr Leu Leu Phe Leu Leu Leu Pro Val Ala
-18             -15                 -10                 -5

Ala Ser Gln Thr Ser Ala Gly Ser Cys Ser Gly Cys Gly Thr Leu Ser
        1                   5                   10

Leu Pro Leu Leu Ala Gly Leu Val Ala Ala Asp Ala Val Met Ser Leu
15                  20                  25                  30

Leu Ile Val Gly Val Val Phe Val Cys Met Arg Pro His Gly Arg Pro
                35                  40                  45

Ala Gln Glu Asp Gly Arg Val Tyr Ile Asn Met Pro Gly Arg Gly
            50                  55                  60

(2) INFORMATION FOR SEQ ID NO: 11:

(i) SEQUENCE CHARACTERISTICS:
              (A) LENGTH: 996 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: CDS (B) LOCATION: 157..717

(xi) SEQUENCE DESCRIPTION: SEQ ID NO: 11:

| | |
|---|---:|
| GGCTTAGCGT GGTCGCGGCC GAGGTGGCAA AAGGAGCATA TTCTCAGGAG ACGGGGCCCC | 60 |
| TGCCTGCCAC ACCAAGCATT AGGCCACCAG GAAGACCCCC ATCTGCAAGC AAGCCTAGCC | 120 |
| TTCCAGGGAG AAAGAGGCCT CTGCAGCTCC TTCATC ATG AAC TGG CAC ATG ATC<br>                                                                     Met Asn Trp His Met Ile<br>                                                                       1               5 | 174 |
| ATC TCT GGG CTT ATT GTG GTA GTG CTT AAA GTT GTT GGA ATG ACC TTA<br>Ile Ser Gly Leu Ile Val Val Val Leu Lys Val Val Gly Met Thr Leu<br>                10                       15                    20 | 222 |
| TTT CTA CTT TAT TTC CCA CAG ATT TTT AAC AAA AGT AAC GAT GGT TTC<br>Phe Leu Leu Tyr Phe Pro Gln Ile Phe Asn Lys Ser Asn Asp Gly Phe<br>        25                       30                       35 | 270 |
| ACC ACC ACC AGG AGC TAT GGA ACA GTC TCA CAG ATT TTT GGG AGC AGT<br>Thr Thr Thr Arg Ser Tyr Gly Thr Val Ser Gln Ile Phe Gly Ser Ser<br> 40                       45                       50 | 318 |
| TCC CCA AGT CCC AAC GGC TTC ATT ACC ACA AGG AGC TAT GGA ACA GTC<br>Ser Pro Ser Pro Asn Gly Phe Ile Thr Thr Arg Ser Tyr Gly Thr Val<br>55                  60                       65                   70 | 366 |
| TGC CCC AAA GAC TGG GAA TTT TAT CAA GCA AGA TGT TTT TTC TTA TCC<br>Cys Pro Lys Asp Trp Glu Phe Tyr Gln Ala Arg Cys Phe Phe Leu Ser<br>              75                       80                      85 | 414 |
| ACT TCT GAA TCA TCT TGG AAT GAA AGC AGG GAC TTT TGC AAA GGA AAA<br>Thr Ser Glu Ser Ser Trp Asn Glu Ser Arg Asp Phe Cys Lys Gly Lys<br>              90                       95                    100 | 462 |
| GGA TCC ACA TTG GCA ATT GTC AAC ACG CCA GAG AAA CTG TTT CTT CAG<br>Gly Ser Thr Leu Ala Ile Val Asn Thr Pro Glu Lys Leu Phe Leu Gln<br>       105                     110                    115 | 510 |
| GAC ATA ACT GAT GCT GAG AAG TAT TTT ATT GGC TTA ATT TAC CAT CGT<br>Asp Ile Thr Asp Ala Glu Lys Tyr Phe Ile Gly Leu Ile Tyr His Arg<br>120                  125                     130 | 558 |
| GAA GAG AAA AGG TGG CGT TGG ATC AAC AAC TCT GTG TTC AAT GGC AAT<br>Glu Glu Lys Arg Trp Arg Trp Ile Asn Asn Ser Val Phe Asn Gly Asn<br>135                 140                    145                  150 | 606 |
| GTT ACC AAT CAG AAT CAG AAT TTC AAC TGT GCG ACC ATT GGC CTA ACA<br>Val Thr Asn Gln Asn Gln Asn Phe Asn Cys Ala Thr Ile Gly Leu Thr<br>               155                    160                    165 | 654 |
| AAG ACC TTT GAT GCT GCA TCA TGT GAC ATC AGC TAC CGC AGG ATC TGT<br>Lys Thr Phe Asp Ala Ala Ser Cys Asp Ile Ser Tyr Arg Arg Ile Cys<br>       170                     175                    180 | 702 |
| GAG AAG AAT GCC AAA TGATCACAGT TCCCTGTGAC AAGAACTATA CTTGCAACTC<br>Glu Lys Asn Ala Lys<br>             185 | 757 |
| TTTTTGAATC CATAACAGGT CGTACTGGCC AATGATTACT TTTACTTACC TATCTGTACT | 817 |
| ACCAGTAGCG GTCCTTGCCC ATTTGGGAAA CTGAGCTTCT TTCTTCTGCA CTGGGGGACT | 877 |
| GGATGCTAGC CATCTCCAGG AGACAGGATC AGTTTTACGG AAACAACTCA GTTAGTATAG | 937 |
| AGATGAGGTC CGCTTCTGTA GTACCTTCCT TCAAATAAAG AAATTTGGTA CCTGCCCGG | 996 |

(2) INFORMATION FOR SEQ ID NO: 12:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Asn Trp His Met Ile Ile Ser Gly Leu Ile Val Val Leu Lys
 1               5                  10                  15

Val Val Gly Met Thr Leu Phe Leu Leu Tyr Phe Pro Gln Ile Phe Asn
             20                  25                  30

Lys Ser Asn Asp Gly Phe Thr Thr Thr Arg Ser Tyr Gly Thr Val Ser
         35                  40                  45

Gln Ile Phe Gly Ser Ser Pro Ser Pro Asn Gly Phe Ile Thr Thr
     50                  55                  60

Arg Ser Tyr Gly Thr Val Cys Pro Lys Asp Trp Glu Phe Tyr Gln Ala
 65              70                  75                  80

Arg Cys Phe Phe Leu Ser Thr Ser Glu Ser Ser Trp Asn Glu Ser Arg
                 85                  90                  95

Asp Phe Cys Lys Gly Lys Gly Ser Thr Leu Ala Ile Val Asn Thr Pro
            100                 105                 110

Glu Lys Leu Phe Leu Gln Asp Ile Thr Asp Ala Glu Lys Tyr Phe Ile
            115                 120                 125

Gly Leu Ile Tyr His Arg Glu Glu Lys Arg Trp Arg Trp Ile Asn Asn
130                 135                 140

Ser Val Phe Asn Gly Asn Val Thr Asn Gln Asn Gln Asn Phe Asn Cys
145                 150                 155                 160

Ala Thr Ile Gly Leu Thr Lys Thr Phe Asp Ala Ala Ser Cys Asp Ile
                165                 170                 175

Ser Tyr Arg Arg Ile Cys Glu Lys Asn Ala Lys
                180                 185

(2) INFORMATION FOR SEQ ID NO: 13:

(i) SEQUENCE CHARACTERISTICS:
        (A) LENGTH: 896 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 140..709

(ix) FEATURE:
        (A) NAME/KEY: misc_feature
        (B) LOCATION: 221
        (D) OTHER INFORMATION: /note= "short form variant lacks
            nucleotides 221-295"

(ix) FEATURE:
        (A) NAME/KEY: misc_feature
        (B) LOCATION: 29
        (D) OTHER INFORMATION: /note= "short form variant
            difference at nucleotides 29-35 reads CAGAAGA; 107-109
            reads AGA; 128-129 reads AT; 820-826 reads CATAGGT; lacks
            859; and 879-880 reads CA"

(xi) SEQUENCE DESCRIPTION: SEQ ID NO: 13:

AGGACATTAC CGAGCAGGAG CATACATTTC CAGAGCAAGG AGCCCTGCTC GCTGCACCGA        60

ATATCTTATC AAAAAGACTC CTATCTGTAT GCCAACCCAG ACTTCCCAGA AGAGATCAGA      120

TCCCTGATCC CCATCATC ATG AAC TGG CAC ATG ATC ATC TCG GGG CTT ATC        172
                    Met Asn Trp His Met Ile Ile Ser Gly Leu Ile
                     1               5                      10

GTA GTA GTG ATC AAA GTT GTT GGA ATG ACC TTT TTT CTG CTG TAT TTC        220
Val Val Val Ile Lys Val Val Gly Met Thr Phe Phe Leu Leu Tyr Phe
            15                  20                  25
```

```
CCA CAG GTT TTT GGC AAA AGT AAT GAT GGC TTC GTC CCC ACG GAG AGC       268
Pro Gln Val Phe Gly Lys Ser Asn Asp Gly Phe Val Pro Thr Glu Ser
            30                  35                  40

TAC GGA ACC ACT AGT GTG CAG AAT GTC TCA CAG ATC TTT GGG AGA AAT       316
Tyr Gly Thr Thr Ser Val Gln Asn Val Ser Gln Ile Phe Gly Arg Asn
        45                  50                  55

GAC GAA AGT ACC ATG CCT ACA AGG AGC TAT GGA ACA GTC TGT CCC AGA       364
Asp Glu Ser Thr Met Pro Thr Arg Ser Tyr Gly Thr Val Cys Pro Arg
60                  65                  70                  75

AAC TGG GAT TTT CAC CAA GGA AAA TGC TTT TTC TTC TCC TTC TCC GAA       412
Asn Trp Asp Phe His Gln Gly Lys Cys Phe Phe Phe Ser Phe Ser Glu
                80                  85                  90

TCA CCT TGG AAA GAC AGC ATG GAT TAT TGT GCA ACA CAA GGA TCC ACA       460
Ser Pro Trp Lys Asp Ser Met Asp Tyr Cys Ala Thr Gln Gly Ser Thr
            95                  100                 105

CTG GCA ATT GTC AAC ACT CCA GAG AAA CTG AAG TAT CTT CAG GAC ATA       508
Leu Ala Ile Val Asn Thr Pro Glu Lys Leu Lys Tyr Leu Gln Asp Ile
        110                 115                 120

GCT GGT ATT GAG AAT TAC TTT ATT GGT TTG GTA CGT CAG CCT GGA GAG       556
Ala Gly Ile Glu Asn Tyr Phe Ile Gly Leu Val Arg Gln Pro Gly Glu
125                 130                 135

AAA AAG TGG CGC TGG ATC AAC AAC TCT GTG TTC AAT GGC AAT GTT ACC       604
Lys Lys Trp Arg Trp Ile Asn Asn Ser Val Phe Asn Gly Asn Val Thr
140                 145                 150                 155

AAT CAG GAC CAG AAC TTC GAC TGT GTC ACT ATA GGT CTG ACG AAG ACA       652
Asn Gln Asp Gln Asn Phe Asp Cys Val Thr Ile Gly Leu Thr Lys Thr
                160                 165                 170

TAT GAT GCT GCA TCA TGT GAA GTC AGC TAT CGC TGG ATC TGC GAA ATG       700
Tyr Asp Ala Ala Ser Cys Glu Val Ser Tyr Arg Trp Ile Cys Glu Met
            175                 180                 185

AAT GCC AAA TGATCATAGA TCTCTACAAG AGTGAATTTT TACAGAGCTA               749
Asn Ala Lys
        190

GCAAAGGAGA TTAGTTGTGA CTGAAACCAG CCCAGGAAAA TATAGAGCAT CAAAGACTGT     809

GCCCATCTTC ATAGGTGGGA GTTCCCTATT GAATCCTCAA AGTCAATTTT GTTACTCCAC     869

AAACATCTTA CCATAGTAAA ACTCCCT                                         896

(2) INFORMATION FOR SEQ ID NO: 14:

(i) SEQUENCE CHARACTERISTICS:
        (A) LENGTH: 190 amino acids
        (B) TYPE: amino acid
        (D) TOPOLOGY: linear (ii) MOLECULE TYPE: protein (xi) SEQUENCE DESCRIPTION: SEQ ID NO: 14:

Met Asn Trp His Met Ile Ile Ser Gly Leu Ile Val Val Val Ile Lys
1               5                   10                  15

Val Val Gly Met Thr Phe Phe Leu Leu Tyr Phe Pro Gln Val Phe Gly
            20                  25                  30

Lys Ser Asn Asp Gly Phe Val Pro Thr Glu Ser Tyr Gly Thr Thr Ser
        35                  40                  45

Val Gln Asn Val Ser Gln Ile Phe Gly Arg Asn Asp Glu Ser Thr Met
    50                  55                  60

Pro Thr Arg Ser Tyr Gly Thr Val Cys Pro Arg Asn Trp Asp Phe His
65                  70                  75                  80

Gln Gly Lys Cys Phe Phe Phe Ser Phe Ser Glu Ser Pro Trp Lys Asp
```

-continued

```
                        85                      90                      95
Ser Met Asp Tyr Cys Ala Thr Gln Gly Ser Thr Leu Ala Ile Val Asn
            100                     105                 110

Thr Pro Glu Lys Leu Lys Tyr Leu Gln Asp Ile Ala Gly Ile Glu Asn
            115                     120                 125

Tyr Phe Ile Gly Leu Val Arg Gln Pro Gly Glu Lys Lys Trp Arg Trp
            130                     135                 140

Ile Asn Asn Ser Val Phe Asn Gly Asn Val Thr Asn Gln Asp Gln Asn
145                     150                     155                 160

Phe Asp Cys Val Thr Ile Gly Leu Thr Lys Thr Tyr Asp Ala Ala Ser
                165                     170                 175

Cys Glu Val Ser Tyr Arg Trp Ile Cys Glu Met Asn Ala Lys
                180                     185                 190
```

ANTIBODIES AND FRAGMENTS THEREOF TO MDL-1 PROTEIN

This is a Divisional of U.S. Ser. No. 09/127,946, filed Jul. 31, 1998, now U.S. Pat. No. 6,416,973, issued Jul. 9, 2002, which claims benefit of U.S. Provisional Patent Application 60/089,168, filed Jun. 12, 1998; 60/069,639, filed Dec. 15, 1997; 60/063,717, filed Oct. 29, 1997; 60/069,692, filed Dec. 16, 1997; and 60/054,430, filed Aug. 1, 1997; each of which is incorporated herein by reference.

FIELD OF THE INVENTION

The present invention relates to various biological reagents which are useful in modulating a mammalian cellular response, e.g., immune signaling. More particularly, it is directed towards compositions and methods useful in immune cell interactions, e.g., between B and T cells, NK, etc.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed. 1993) *Fundamental Immunology* (3d ed.) Raven Press, N.Y.

The activation of resting T cells is critical to most immune responses and allows these cells to exert their regulatory or effector capabilities. See Paul (ed; 1993) *Fundamental Immunology* 3d ed., Raven Press, N.Y. Increased adhesion between T cells and antigen presenting cells (APC) or other forms of primary stimuli, e.g., immobilized monoclonal antibodies (mAb), can potentiate the T-cell receptor signals. T-cell activation and T cell expansion depends upon engagement of the T-cell receptor (TCR) and co-stimulatory signals provided by accessory cells. See, e.g., Jenkins and Johnson (1993) *Curr. Opin. Immunol.* 5:361–367; Bierer and Hahn (1993) *Semin. Immunol.* 5:249–261; June, et al. (1990) *Immunol. Today* 11:211–216; and Jenkins (1994) *Immunity* 1:443–446. A major, and well-studied, co-stimulatory interaction for T cells involves either CD28 or CTLA-4 on T cells with either B7 or B70 (Jenkins (1994) *Immunity* 1:443–446). Recent studies on CD28 deficient mice (Shahinian, et al. (1993) *Science* 261:609–612; Green, et al. (1994) *Immunity* 1:501–508) and CTLA-4 immunoglobulin expressing transgenic mice (Ronchese, et al. (1994) *J. Exp. Med.* 179:809–817) have revealed deficiencies in some T-cell responses though these mice have normal primary immune responses and normal CTL responses to lymphocytic choriomeningitis virus and vesicular stomatitis virus. As a result, both these studies conclude that other co-stimulatory molecules must be supporting T-cell function. However, identification of these molecules which mediate distinct costimulatory signals has been difficult.

Moreover, similar negative and positive signaling occurs with lymphocytes (LIRs); natural killer cells (KIRs), and other cell types (ILT, and CD94). See, e.g., Moretta, et al. (1996) *Ann. Rev. Immunol.* 14:619–648; Malissen (1996) *Nature* 384:518–519; Scharenberg and Kinet (1996) *Cell* 87:961–964; Colonna, et al. (1995) *Science* 268:405408; Wagtmann, et al. (1995) *Immunity* 2:439–449; D'Andrea, et al. (1995) *J. Immunol.* 155:2306–2310; Samaridis and Colonna (1997) *Eur. J. Immunol.* 27:660–665; Aramburu, et al. (1990) *J. Immunol.* 144:3238–3247; Aramburu, et al. (1991) *J. Immunol.* 147:714–721; and Rubio, et al. (1993) *J. Immunol.* 151:1312–1321.

The inability to modulate activation signals prevents control of inappropriate developmental or physiological responses in the immune system. The present invention provides at least one alternative costimulatory molecule, agonists and antagonists of which will be useful in modulating a plethora of immune responses.

SUMMARY OF THE INVENTION

The present invention is based on the discovery of particular genes involved in cell signaling. Various genes have been identified which interact with gene forms whose function was not understood. These are the DNAX Accessory Protein, 12 kD (DAP12); the DNAX Accessory Protein, 10 kD (DAP10); and another associated accessory protein, the MDL-1.

Particular embodiments of the invention include a substantially pure or recombinant polypeptide exhibiting identity over a length of at least about 12 amino acids to the mature polypeptide from: SEQ ID NO: 2 or 6; SEQ ID NO: 8 or 10; or SEQ ID NO: 12 or 14. Preferably, the SEQ ID NO: is 2 or 6; and the polypeptide: is a mature natural sequence DAP12 of SEQ ID NO:2 or 6; comprises an ITAM motif; or comprises a charged residue in a transmembrane domain; or the SEQ ID NO: is 8 or 10, and the polypeptide: is a mature natural sequence DAP10 of SEQ ID NO: 6 or 10; comprises an ITIM motif; or comprises a charged residue in a transmembrane domain; or the SEQ ID NO: is 12 or 14, and the polypeptide: is a mature natural sequence MDL-1 of SEQ ID NO: 12 or 14; or comprises a charged residue in a transmembrane domain. Other preferred embodiments include such a polypeptide which: comprises a plurality of the lengths; is a natural allelic variant of DAP12; is a natural allelic variant of DAP10; is a natural allelic variant of MDL-1; has a length at least about 30 amino acids; is a synthetic polypeptide; is attached to a solid substrate: is conjugated to another chemical moiety; is a 5-fold or less substitution from natural sequence; or is a deletion or insertion variant from a natural sequence. Other preferred embodiments include a composition comprising: a sterile DAP12 polypeptide; the DAP12 polypeptide and a carrier, wherein the carrier is: an aqueous compound, including water, saline, and/or buffer; and/or formulated for oral, rectal, nasal, topical, or parenteral administration; or a sterile DAP10 polypeptide; or the DAP10 polypeptide and a carrier, wherein the carrier is: an aqueous compound, including water, saline, and/or buffer; and/or formulated for oral, rectal, nasal, topical, or parenteral administration; or a sterile MDL-1 polypeptide; or the MDL-1 polypeptide and a carrier, wherein the carrier is: an aqueous compound, including water, saline, and/or buffer; and/or formulated for oral, rectal, nasal, topical, or parenteral administration.

A fusion protein is provided, comprising such a polypeptide and: a detection or purification tag, including a FLAG, His6, or immunoglobulin peptide; bacterial β-galactosidase, trpE, Protein A, β-lactamase, alpha amylase, alcohol dehydrogenase, and yeast alpha mating factor; or sequence of another membrane protein.

Kits are provided comprising such a polypeptide and: a compartment comprising the polypeptide; and/or instructions for use or disposal of reagents in the kit.

Binding compounds are also provided, comprising an antigen binding portion from an antibody, which specifically binds to: a natural DAP12 polypeptide, wherein the antibody: is raised against a mature polypeptide of SEQ ID NO:2 or 6: is immunoselected; is a polyclonal antibody; binds to a denatured DAP12; exhibits a Kd to antigen of at least 30 μM; is attached to a solid substrate, including a bead or plastic membrane; is in a sterile composition; or is detectably labeled, including a radioactive or fluorescent label; or a natural DAP10 polypeptide, wherein the antibody: is raised against a mature polypeptide of SEQ ID NO: 8 or 10; is immunoselected; is a polyclonal antibody; binds to a denatured DAP10; exhibits a Kd to antigen of at least 30 μM; is attached to a solid substrate, including a bead or plastic membrane; is in a sterile composition; or is detectably labeled, including a radioactive or fluorescent label; or a natural MDL-1 polypeptide, wherein the antibody: is raised against a mature polypeptide of SEQ ID NO: 12 or 14; is immunoselected; is a polyclonal antibody; binds to a denatured MDL-1; exhibits a Kd to antigen of at least 30 μM; is attached to a solid substrate, including a bead or plastic membrane; is in a sterile composition; or is detectably labeled, including a radioactive or fluorescent label. Various kits are provided, e.g., comprising the binding compound, and: a compartment comprising the binding compound; and/or instructions for use or disposal of reagents in the kit. Additional embodiments include a composition comprising: a sterile binding compound, or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding these polypeptides, wherein the nucleic acid encodes an antigenic peptide sequence of SEQ ID NO: 2, 6, 8, 10, 12, or 14. Preferred embodiments include such a nucleic acid, which encodes a plurality of antigenic peptide sequences of the table. Other nucleic acids include one which: is an expression vector; further comprises an origin of replication; is from a natural source; comprises a detectable label; comprises synthetic nucleotide sequence; is less than 6 kb, preferably less than 3 kb; is from a mammal, including a primate or rodent; comprises a natural full length coding sequence; is a hybridization probe for a gene encoding DAP12, DAP10, or MDL-1: or is a PCR primer, PCR product, or mutagenesis primer.

Other nucleic acids include ones which hybridize under stringent wash conditions of at least 50° C., less than 400 mM salt, and 50% formamide to: SEQ ID NO: 1 or 5; SEQ ID NO: 7 or 9; or SEQ ID NO: 11 or 13. The invention provides a cell or tissue comprising such a recombinant nucleic acid, including where the cell is: a prokaryotic cell; a eukaryotic cell; a bacterial cell; a yeast cell; an insect cell; a mammalian cell; a mouse cell; a primate cell; or a human cell. Certain kits include one comprising the nucleic acid, and: a compartment comprising the nucleic acid; a compartment further comprising a DAP12, DAP10, or MDL-1; polypeptide; and/or instructions for use or disposal of reagents in the kit. Preferred nucleic acids include ones which: exhibit identity over a stretch of at least about 30 nucleotides to a primate DAP12; exhibit identity over a stretch of at least about 30 nucleotides to a primate DAP10; exhibit identity over a stretch of at least about 30 nucleotides to a primate MDL-1; and/or further encode a KIR, ILT/MIR or CD94/NKG2C receptor. Preferred embodiments include those wherein: the wash conditions are at 60° C. and/or 200 mM salt; or the stretch is at least 55 nucleotides.

The invention also provides methods of modulating physiology or development of a cell or tissue culture cells comprising contacting the cell with an agonist or antagonist of a DAP12, DAP10, or MDL-1. Also, methods are provided of screening for a compound which blocks interaction of a DAP12 or DAP10 with a KIR, ILT/MIR, or CD94/NKG2C receptor, comprising contacting the compound to the DAP12 or DAP10 in the presence of the receptor.

DETAILED DESCRIPTION OF THE PREFERRED EMBODIMENTS

Outline
I. General
II. Purified Human DAP and MDL
   A. physical properties
   B. biological properties
III. Physical Variants
   A. sequence variants, fragments
   B. post-translational variants
      1. glycosylation
      2. others
IV. Functional Variants
   A. analogs; fragments
      1. agonists
      2. antagonists
   B. mimetics
      1. protein
      2. chemicals
   C. polymorphic variants
V. Antibodies
   A. polyclonal
   B. monoclonal
   C. fragments, binding compositions
VI. Nucleic Acids
   A. natural isolates; methods
   B. synthetic genes
   C. methods to isolate
VII. Making DAP12; Mimetics
   A. recombinant methods
   B. synthetic methods
   C. natural purification
VIII. Uses
   A. diagnostic
   B. therapeutic
IX. Kits
   A. nucleic acid reagents
   B. protein reagents
   C. antibody reagents
X. Ligand or Counterreceptor.
I. General The present invention provides the amino acid sequences and DNA sequences of mammalian proteins which exhibit properties of accessory molecules for cellular activation antigens. One protein is designated DNAX Activation Protein, 12 kD (DAP12). The primate sequence described herein was obtained from sequences identified from various databases. Similar sequences for proteins in other mammalian species should also be available, including rodent. The descriptions below are directed, for exemplary purposes, to the human DAP12 natural allele described, but are likewise applicable to allelic and/or polymorphic variants, e.g., from other individuals, as well as splicing variants, e.g., natural forms.

A second protein is designated DNAX Activation protein, 10 kD (DAP10), which exhibits many similar structural and biological features. A third protein associates with the DAP12, and possibly with the DAP10, and is designated Myeloid DAP12 associated Lectin-1 (MDL-1).

These genes will allow isolation of other primate or mammalian genes encoding proteins related to them, further extending the family beyond the specific embodiments described. The procedure is broadly set forth below.

The DNAX Activation Protein 12 kD (DAP12) is so named because of its structural features, and presumed function. Certain cell surface receptors lack intrinsic functionality, which hypothetically may interact with another protein partner, suggested to be a 12 kD protein. The mechanism of the signaling may involve an ITAM signal.

The DAP12 was identified from sequence databases based upon a hypothesized relationship to CD3 (see Olcese, et al. (1997) *J. Immunol.* 158:5083–5086), the presence of an ITIM sequence (see Thomas (1995) *J. Exp. Med.* 181:1953–1956), certain size predictions (see Olcese; and Takase, et al. (1997) *J. Immunol.* 159:741–747, and other features. In particular, the transmembrane domain was hypothesized to contain a charged residue, which would allow a salt bridge with the corresponding transmembrane segments of its presumed receptor partners, KIR (killer cell inhibitory molecules) CD94 protein, and possibly other similar proteins. See Daeron, et al. (1995) *Immunity* 3:635–646.

In fact, many of the known KIR, MIR, ILT, and CD94/NKG2 receptor molecules may actually function with an accessory protein which is part of the functional receptor complex. See Olcese, et al. (1997) *J. Immunol.* 158:5083–5086; and Takase, et al. (1997) *J. Immunol.* 159:741–747. Thus, the invention provides purified forms of the functional signaling receptors, e.g., the DAP12 and/or DAP10 with the other subunit. See, e.g., Daeron, et al. (1995) *Immunity* 3:635–646. Thus, a combination of DAP12 or DAP10 with another receptor forms a functional complex on one cell which is a receptor complex for a counter receptor or ligand for the complex.

The DAP10 was identified partly by its homology to the DAP12, and other features. In particular, in contrast to the DAP12, which exhibits an ITAM activation motif, the DAP10 exhibits an ITIM inhibitory motif. The MDL-1 was identified by its functional association with DAP12.

Moreover, the functional interaction between, e.g., DAP12 or DAP10, and its accessory receptor may allow use of the structural combination in receptors which normally are not found in a truncated receptor form. Thus, the mechanism of signaling through such accessory proteins as the DAP12 and DAP10 allow for interesting engineering of other KIR-like receptor complexes, e.g., with the KIR, MIR, ILT, and CD94 NKG2 type receptors. Truncated forms of intact receptors may be constructed which interact with a DAP12 or DAP10 to form a functional signaling complex.

The primate and rodent forms exhibit significant sequence identity when aligned. See, e.g., Tables 1, 2, and 3. Other genes exhibit much lower identity over the entire mature coding region, though some exhibit higher identity in particular segments.

II Purified DAP and MDL

Table 1 discloses both the nucleotide sequence (SEQ ID NO: 1 and 5) of the cDNA and the corresponding amino acid sequence for DAP12 embodiments. The primate nucleotide sequence corresponds to SEQ ID NO: 1; the amino acid sequence corresponds to SEQ ID NO: 2. The signal sequence appears to run from met(−26) to gln(−1) or ala1; the mature protein should run from about ala1 (or gln2), the extracellular domain from about ala1 to pro14; the extracellular domain contains two cysteines at 7 and 9, which likely allow disulfide linkages to additional homotypic or heterotypic accessory proteins; the transmembrane region runs from about gly15 or val16 to about gly39; and an ITAM motif from tyr65 to leu79 (YxxL-6/8x-YxxL). The LVA03A EST was identified and used to extract other overlapping sequences. See also Genbank Human ESTs that are part of human DAP12; some, but not all, inclusive Genbank Accession # AA481924; H39980; W60940; N41026; R49793; W80864; W92376; H12338; T52100; AA480109; H12392; W74783; and T55959.

TABLE 1

Primate DAP12 cDNA identified from human cDNA library.
SEQ ID NO: 1 and 2. Actual signal cleavage point may be
slightly different from that indicated, e.g., may be
between ala 1 and gln2.

```
ATG GGG GGA CTT GAA CCC TGC AGC AGG CTC CTG CTC CTG CCT CTC CTG    48
Met Gly Gly Leu Glu Pro Cys Ser Arg Leu Leu Leu Leu Pro Leu Leu
-26 -25              -20                      -15

CTG GCT GTA AGT GGT CTC CGT CCT GTC CAG GCC CAG GCC CAG AGC GAT    96
Leu Ala Val Ser Gly Leu Arg Pro Val Gln Ala Gln Ala Gln Ser Asp
-10              -5                   1                   5

TGC AGT TGC TCT ACG GTG AGC CCG GGC GTG CTG GCA GGG ATC GTG ATG   144
Cys Ser Cys Ser Thr Val Ser Pro Gly Val Leu Ala Gly Ile Val Met
              10                  15                  20

GGA GAC CTG GTG CTG ACA GTG CTC ATT GCC CTG GCC GTG TAC TTC CTG   192
Gly Asp Leu Val Leu Thr Val Leu Ile Ala Leu Ala Val Tyr Phe Leu
          25                  30                  35

GGC CGG CTG GTC CCT CGG GGG CGA GGG GCT GCG GAG GCA GCG ACC CGG   240
Gly Arg Leu Val Pro Arg Gly Arg Gly Ala Ala Glu Ala Ala Thr Arg
        40                  45                  50

AAA CAG CGT ATC ACT GAC ACC GAG TCG CCT TAT CAG GAG CTC CAG GGT   288
Lys Gln Arg Ile Thr Asp Thr Glu Ser Pro Tyr Gln Glu Leu Gln Gly
55                  60                  65                  70
```

TABLE 1-continued

```
CAG AGG TCG GAT GTC TAC AGC GAC CTC AAC ACA CAG AGG CCG TAT TAC    336
Gln Arg Ser Asp Val Tyr Ser Asp Leu Asn Thr Gln Arg Pro Tyr Tyr
            75                  80                  85

AAA TGA                                                            342
Lys
``` contig sequence with flanking untranslated regions
(less reliable; possible sequence errors; SEQ ID NO: 3)

CTTGCCTGGACGCTGCGCCACATCCCACCGGCCCTTACACTGTGGTGTCCAGCAGCATCCGGCTTCATGGGGGA

CTTGAACCCTGCAGCAGGCTCCTGCTCCTGCCTCTCCTGCTGGCTGTAAGTGGTCTCCGTCCTGTCCAGGCCCAG

GCCCAGAGCGATTGCAGTTGCTCTACGGTGAGCCCGGGCGTGCTGGCAGGGATCGTGATGGGAGACCTGGTGCTG

ACAGTGCTCATTGCCCTGGCCGTGTACTTCCTGGGCCGGCTGGTCCCTCGGGGGCGAGGGGCTGCGGAGGCAgcG

ACCCGGAAACAGCGTATCACTGAGACCGAGTCGCCTTATCAGGAGCTCCAGGGTCAGAGGTCGGATGTCTACAGC

GACCTCAACACACAGAGGCCGTATTACAAATGAGCCCGAATCATGACAGTCAGCAACATGATAcCTGGATCCAGC

CATTCcTGAAGCCCAnCCTGCAcCTCATTCCAACTCCTACCGCGATACAGACCCACAGAGTGCCATCCCTGaGAG

ACCAGACCGCTCCCCAATACTCTCCTAAAATAAACATGAAGCACaAAAAAAAAAAAAAAAAAAAACTCnGGGGGGG

GGCCCGGTTAnCCAATTTGGnCCTAAAG

Rodent DAP12 cDNAs, see mouse ESTs Genbank numbers
AA24315; W91184; AA098506; AA13806; W88159; and W41142.
A consensus sequence, with filling in of holes, is well
within the level of skill in the art. See SEQ ID NO:5 and 6.
Signal cleavage point may be to either side.

```
ATG GGG GCT CTG GAG CCC TCC TGG TGC CTT CTG TTC CTT CCT GTC CTC    48
Met Gly Ala Leu Glu Pro Ser Trp Cys Leu Leu Phe Leu Pro Val Leu
-26 -25                 -20                 -15

CTG ACT GTG GGA GGA TTA AGT CCC GTA CAG GCC CAG AGT GAC ACT TTC    96
Leu Thr Val Gly Gly Leu Ser Pro Val Gln Ala Gln Ser Asp Thr Phe
-10              -5                   1                   5

CCA AGA TGC GAC TGT TCT TCC GTG AGC CCT GGT GTA CTG GCT GGG ATT   144
Pro Arg Cys Asp Cys Ser Ser Val Ser Pro Gly Val Leu Ala Gly Ile
                10                  15                  20

GTT CTG GGT GAC TTG GTG TTG ACT CTG CTG ATT GCC CTG GCT GTG TAC   192
Val Leu Gly Asp Leu Val Leu Thr Leu Leu Ile Ala Leu Ala Val Tyr
            25                  30                  35

TCT CTG GGC CGC CTG GTC TCC CGA GGT CAA GGG ACA GCG GAA GGG ACC   240
Ser Leu Gly Arg Leu Val Ser Arg Gly Gln Gly Thr Ala Glu Gly Thr
        40                  45                  50

CGG AAA CAA CAC ATT GCT GAG ACT GAG TCG CCT TAT CAG GAG CTT CAG   288
Arg Lys Gln His Ile Ala Glu Thr Glu Ser Pro Tyr Gln Glu Leu Gln
 55                  60                  65                  70

GGT CAG AGA CCA GAA GTA TAC AGT GAC CTC AAC ACA CAG AGG CAA TAT   336
Gly Gln Arg Pro Glu Val Tyr Ser Asp Leu Asn Thr Gln Arg Gln Tyr
            75                  80                  85

TAC AGA TGA                                                       345
Tyr Arg
```

Alignment of primate and rodent
DAP12 protein sequences (SEQ ID NO: 2 and 4).

```
h     MGGLEPCSRL LLLPLLLAVS GLRPVQAQAQ S--DCSCSTV SPGVLAGIVM
m     MGALEPSWCL LFLPVLLTVG GLSPVQAQSD TFPRCDCSSV SPGVLAGIVL h     GDLVLTVLIA LAVYFLGRLV PRGRGAAEAA TRKQRITETE SPYQELQGQR
m     GDLVLTLLIA LAVYSLGRLV SRGQGTAEG- TRKQHIAETE SPYQELQGQR h     SDVYSDLNTQ RPYYK*
m     PEVYSDLNTQ RQYYR*
```

Table 2 discloses both the nucleotide sequence of the cDNA and the corresponding amino acid sequence (SEQ ID NO: 7, 8, 9, and 10) of each of the human and mouse DAP10 genes. The nucleotide sequence for human corresponds to SEQ ID NO: 7; the amino acid sequence corresponds to SEQ ID NO: 8. The signal sequence appears to run from about met(−18) to ala(−1); the mature protein should run from about gln1, the extracellular domain from about gln1 to pro30; the extracellular domain contains two cysteines at 21 and 24, which likely allow disulfide linkages to additional homotypic or heterotypic accessory proteins; the transmembrane region runs from about leu31 to val47, with a characteristic charged residue corresponding to asp39; and an interesting YxxM motif from tyr67 to met70, which is similar to that seen in CD28, CTLA-4, and CD19.

Similarly, for the mouse DAP10, the signal sequence appears to run from about met(−18) to ser(−1); the mature protein should run from about gln1, the extracellular domain from about gln1 to pro16; the extracellular domain contains two cysteines at 7 and 10, which likely allow disulfide linkages to additional homotypic or heterotypic accessory proteins; the transmembrane region runs from about leu17 to val33, with a characteristic charged residue corresponding to asp25; and an interesting YxxM motif from tyr54 to met57, which is similar to that seen in CD28 and CTLA-4.

TABLE 2

Primate DAP10 cDNA identified from human cDNA library. See SEQ ID NO: 7 and 8.

```
GTCGACCTGG ACTTCTCTGG ACCACAGTCC TCTGCCAGAC CCCTGCCAGA CCCCAGTCCA         60

CC ATG ATC CAT CTG GGT CAC ATC CTC TTC CTG CTT TTG CTC CCA GTG          107
   Met Ile His Leu Gly His Ile Leu Phe Leu Leu Leu Leu Pro Val
   -18             -15                 -10                  -5

GCT GCA GCT CAG ACG ACT CCA GGA GAG AGA TCA TCA CTC CCT GCC TTT        155
Ala Ala Ala Gln Thr Thr Pro Gly Glu Arg Ser Ser Leu Pro Ala Phe
            1               5                   10

TAC CCT GGC ACT TCA GGC TCT TGT TCC GGA TGT GGG TCC CTC TCT CTG        203
Tyr Pro Gly Thr Ser Gly Ser Cys Ser Gly Cys Gly Ser Leu Ser Leu
        15              20              25

CCG CTC CTG GCA GGC CTC GTG GCT GCT GAT GCG GTG GCA TCG CTG CTC        251
Pro Leu Leu Ala Gly Leu Val Ala Ala Asp Ala Val Ala Ser Leu Leu
30              35              40              45

ATC GTG GGG GCG GTG TTC CTG TGC GCA CGC CCA CGC CGC AGC CCC GCC        299
Ile Val Gly Ala Val Phe Leu Cys Ala Arg Pro Arg Arg Ser Pro Ala
                50              55              60

CAA GAT GGC AAA GTC TAC ATC AAC ATG CCA GGC AGG GGC TGACCCTCCT         348
Gln Asp Gly Lys Val Tyr Ile Asn Met Pro Gly Arg Gly
            65                  70

GCAGCTTGGA CCTTTGACTT CTGACCCTCT CATCCTGGAT GGTGTGTGGT GCACAGGAAA      408

CCCCGCCCCA ACTTTTGGAT TGTAATAAAA CATTTGAAAC ACA                         451
```

Rodent DAP10 cDNA sequence from mouse library.
See SEQ ID NO: 9 and 10.

```
GTCACCATCG GGGTGACATC CGTCCTAGCT GCCTCTCTTC TCCTCTACTG TTCTGAGGAC        60

TTCCCTGGAC CACAGTTTTG GCCAGATCCC TTCAGGTCCC AGCCCAGC ATG GAC CCC       117
                                                      Met Asp Pro
                                                          -18

CCA GGC TAC CTC CTG TTC CTG CTT CTG CTC CCA GTG GCT GCA AGT CAG       165
Pro Gly Tyr Leu Leu Phe Leu Leu Leu Leu Pro Val Ala Ala Ser Gln
-15                 -10                 -5                    1

ACA TCG GCA GGT TCC TGC TCC GGA TGT GGG ACT CTG TCT CTG CCA CTC       213
Thr Ser Ala Gly Ser Cys Ser Gly Cys Gly Thr Leu Ser Leu Pro Leu
            5               10                  15

CTG GCA GGC CTA GTG GCT GCA GAT GCG GTC ATG TCA CTC CTA ATT GTA       261
Leu Ala Gly Leu Val Ala Ala Asp Ala Val Met Ser Leu Leu Ile Val
            20              25              30

GGG GTG GTG TTT GTA TGT ATG CGC CCA CAC GGC AGG CCT GCC CAA GAA       309
Gly Val Val Phe Val Cys Met Arg Pro His Gly Arg Pro Ala Gln Glu
            35              40              45

GAT GGT AGA GTC TAC ATC AAC ATG CCT GGC AGA GGC TGACCACGGC            355
Asp Gly Arg Val Tyr Ile Asn Met Pro Gly Arg Gly
50                  55                  60
```

TABLE 2-continued

```
ACCTTCTGAC CCGCTCATCC TGGATCCTGT GGGTTTGGGG TGCGTGGG        403
```

Alignment of primate and rodent protein sequences (SEQ ID NO: 8 and 10).

```
h:    MIHLGHILFL LLLPVAAAQT TPGERSSLPA FYPGTSGSCS GCGSLSLPLL
m:    MDPPGYLLFL LLLPVAASQT S--------- -----AGSCS GCGTLSLPLL h:    AGLVAADAVA SLLIVGAVFL CARPRRSPAQ -DGKVYINMP GRG*
m:    AGLVAADAVM SLLIVGVVFV CMRPHGRPAQ EDGRVYINMP GRG*
```

TABLE 3

Primate, e.g., human MDL-1 sequence (SEQ ID NO: 11 and 12).
Because the designated methionine has no upstream termination
codons, as expected, it is conceivable that the protein
actually has additional upstream sequence.
This methionione aligns with mouse sequence (see below).

```
GGCTTAGCGT GGTCGCGGCC GAGGTGGCAA AAGGAGCATA TTCTCAGGAG ACGGGGCCCC    60

TGCCTGCCAC ACCAAGCATT AGGCCACCAG GAAGACCCCC ATCTGCAAGC AAGCCTAGCC   120

TTCCAGGGAG AAAGAGGCCT CTGCAGCTCC TTCATC ATG AAC TGG CAC ATG ATC    174
                                        Met Asn Trp His Met Ile
                                         1               5

ATC TCT GGG CTT ATT GTG GTA GTG CTT AAA GTT GTT GGA ATG ACC TTA    222
Ile Ser Gly Leu Ile Val Val Val Leu Lys Val Val Gly Met Thr Leu
            10              15                  20

TTT CTA CTT TAT TTC CCA CAG ATT TTT AAC AAA AGT AAC GAT GGT TTC    270
Phe Leu Leu Tyr Phe Pro Gln Ile Phe Asn Lys Ser Asn Asp Gly Phe
            25                  30                  35

ACC ACC ACC AGG AGC TAT GGA ACA GTC TCA CAG ATT TTT GGG AGC AGT    318
Thr Thr Thr Arg Ser Tyr Gly Thr Val Ser Gln Ile Phe Gly Ser Ser
        40                  45                  50

TCC CCA AGT CCC AAC GGC TTC ATT ACC ACA AGG AGC TAT GGA ACA GTC    366
Ser Pro Ser Pro Asn Gly Phe Ile Thr Thr Arg Ser Tyr Gly Thr Val
 55                 60                  65                  70

TGC CCC AAA GAC TGG GAA TTT TAT CAA GCA AGA TGT TTT TTC TTA TCC    414
Cys Pro Lys Asp Trp Glu Phe Tyr Gln Ala Arg Cys Phe Phe Leu Ser
                75                  80                  85

ACT TCT GAA TCA TCT TGG AAT GAA AGC AGG GAC TTT TGC AAA GGA AAA    462
Thr Ser Glu Ser Ser Trp Asn Glu Ser Arg Asp Phe Cys Lys Gly Lys
            90                  95                  100

GGA TCC ACA TTG GCA ATT GTC AAC ACG CCA GAG AAA CTG TTT CTT CAG    510
Gly Ser Thr Leu Ala Ile Val Asn Thr Pro Glu Lys Leu Phe Leu Gln
            105                 110                 115

GAC ATA ACT GAT GCT GAG AAG TAT TTT ATT GGC TTA ATT TAC CAT CGT    558
Asp Ile Thr Asp Ala Glu Lys Tyr Phe Ile Gly Leu Ile Tyr His Arg
        120                 125                 130

GAA GAG AAA AGG TGG CGT TGG ATC AAC AAC TCT GTG TTC AAT GGC AAT    606
Glu Glu Lys Arg Trp Arg Trp Ile Asn Asn Ser Val Phe Asn Gly Asn
135                 140                 145                 150

GTT ACC AAT CAG AAT CAG AAT TTC AAC TGT GCG ACC ATT GGC CTA ACA    654
Val Thr Asn Gln Asn Gln Asn Phe Asn Cys Ala Thr Ile Gly Leu Thr
                155                 160                 165

AAG ACC TTT GAT GCT GCA TCA TGT GAC ATC AGC TAC CGC AGG ATC TGT    702
Lys Thr Phe Asp Ala Ala Ser Cys Asp Ile Ser Tyr Arg Arg Ile Cys
            170                 175                 180

GAG AAG AAT GCC AAA TGATCACAGT TCCCTGTGAC AAGAACTATA CTTGCAACTC    757
Glu Lys Asn Ala Lys
            185
```

TABLE 3-continued

```
TTTTTGAATC CATAACAGGT CGTACTGGCC AATGATTACT TTTACTTACC TATCTGTACT      817

ACCAGTAGCG GTCCTTGCCC ATTTGGGAAA CTGAGCTTCT TTCTTCTGCA CTGGGGGACT      877

GGATGCTAGC CATCTCCAGG AGACAGGATC AGTTTTACGG AAACAACTCA GTTAGTATAG      937

AGATGAGGTC CGCTTCTGTA GTACCTTCCT TCAAATAAAG AAATTTGGTA CCTGCCCGG       996
```

Rodent, e.g., mouse, MDL-1 long form sequence
(SEQ ID NO: 13 and 14). A short form variant has been identified,
which has a deletion of nucleotides 221–295. The short form
variant characterized also possesses sequence differences:
nucleotides 29–35 reads CAGAAGA; 107–109 read AGA;
128–129 read AT; 820–826 read CATAGGT; lacks 859; and
879–880 read CA. The initiation methionine has upstream
termination codons suggesting it is the correct amino terminus.

```
AGGACATTAC CGAGCAGGAG CATACATTTC CAGAGCAAGG AGCCCTGCTC GCTGCACCGA        60

ATATCTTATC AAAAGACTC CTATCTGTAT GCCAACCCAG ACTTCCCAGA AGAGATCAGA       120

TCCCTCATCC CCCATCATC  ATG AAC TGG CAC ATG ATC ATC TCG GGG CTT ATC     172
                      Met Asn Trp His Met Ile Ile Ser Gly Leu Ile
                       1               5                      10

GTA GTA GTG ATC AAA GTT GTT GGA ATG ACC TTT TTT CTG CTG TAT TTC        220
Val Val Val Ile Lys Val Val Gly Met Thr Phe Phe Leu Leu Tyr Phe
             15              20                  25

CCA CAG GTT TTT GGC AAA AGT AAT GAT GGC TTC GTC CCC ACG GAG AGC        268
Pro Gln Val Phe Gly Lys Ser Asn Asp Gly Phe Val Pro Thr Glu Ser
         30                  35                  40

TAC GGA ACC ACT AGT GTG CAG AAT GTC TCA CAG ATC TTT GGG AGA AAT        316
Tyr Gly Thr Thr Ser Val Gln Asn Val Ser Gln Ile Phe Gly Arg Asn
     45                  50                  55

GAC GAA AGT ACC ATG CCT ACA AGG AGC TAT GGA ACA GTC TGT CCC AGA        364
Asp Glu Ser Thr Met Pro Thr Arg Ser Tyr Gly Thr Val Cys Pro Arg
 60              65                  70                  75

AAC TGG GAT TTT CAC CAA GGA AAA TGC TTT TTC TTC TCC TTC TCC GAA        412
Asn Trp Asp Phe His Gln Gly Lys Cys Phe Phe Phe Ser Phe Ser Glu
                 80                  85                  90

TCA CCT TGG AAA GAC AGC ATG GAT TAT TGT GCA ACA CAA GGA TCC ACA        460
Ser Pro Trp Lys Asp Ser Met Asp Tyr Cys Ala Thr Gln Gly Ser Thr
             95                 100                 105

CTG GCA ATT GTC AAC ACT CCA GAG AAA CTG AAG TAT CTT CAG GAC ATA        508
Leu Ala Ile Val Asn Thr Pro Glu Lys Leu Lys Tyr Leu Gln Asp Ile
         110                 115                 120

GCT GGT ATT GAG AAT TAC TTT ATT GGT TTG GTA CGT CAG CCT GGA GAG        556
Ala Gly Ile Glu Asn Tyr Phe Ile Gly Leu Val Arg Gln Pro Gly Glu
     125                 130                 135

AAA AAG TGG CGC TGG ATC AAC AAC TCT GTG TTC AAT GGC AAT GTT ACC        604
Lys Lys Trp Arg Trp Ile Asn Asn Ser Val Phe Asn Gly Asn Val Thr
140                 145                 150                 155

AAT CAG GAC CAG AAC TTC GAC TGT GTC ACT ATA GGT CTG ACG AAG ACA        652
Asn Gln Asp Gln Asn Phe Asp Cys Val Thr Ile Gly Leu Thr Lys Thr
                160                 165                 170

TAT GAT GCT GCA TCA TGT GAA GTC AGC TAT CGC TGG ATC TGC GAA ATG        700
Tyr Asp Ala Ala Ser Cys Glu Val Ser Tyr Arg Trp Ile Cys Glu Met
             175                 180                 185

AAT GCC AAA TGATCATAGA TCTCTACAAG AGTGAATTTT TACAGAGCTA                749
Asn Ala Lys
        190

GCAAAGGAGA TTAGTTGTGA CTGAAACCAG CCCAGGAAAA TATAGAGCAT CAAAGACTGT      809

GCCCATCTTC ATAGGTGGGA GTTCCCTATT GAATCCTCAA AGTCAATTTT GTTACTCCAC      869

AAACATCTTA CCATAGTAAA ACTCCCT                                          896
```

TABLE 3-continued

Alignment of human MDL-1 and mouse MDL-1 long form.
Of particular interest are a very short intracellular domain,
corresponding to residues 1–2; with the transmembrane domain
running from about 6 to 27 possessing a charged amino acid at
about residue 16. Three putative N-linked glycosylation sites
correspond to residues 51, 146, and 153 of the mouse long form;
the latter of which are conserved in the human sequence. Note
that the mouse long form, relative to the short form, appears
to contain a spacer segment of about 25 amino acids.

```
hMDL-1      MNWHMIISGLIVVVLKVVGMTLFLLYFPQIFNKSNDGFTTTRSYGT----
mMDL-1      MNWHMIISGLIVVVIKVVGMTFFLLYFPQVFGKSNDGFVPTESYGTTSVQ
            ************.**.*****.*.******..*.**** hMDL-1      -VSQIFGSSSPSPNGFITTRSYGTVCPKDWEFYQARCFFLSTSESSWNES
mMDL-1      NVSQIFGRNDES---TMPTRSYGTVCPRNWDFHQGKCFFFSFSESPWKDS
            ******   *   . *********.*.* * .*** * *** * .* hMDL-1      RDFCKGKGSTLAIVNTPEKL-FLQDITDAEKYFIGLIYHREEKRWRWINN
mMDL-1      MDYCATQGSTLAIVNTPEKLKYLQDIAGIENYFIGLVRQPGEKKWRWINN
            *.*  .*********** .**. * ***.. . .****** hMDL-1      SVFNGNVTNQNQNFNCATIGLTKTFDAASCDISYRRICEKNAK
mMDL-1      SVFNGNVTNQDQNFDCVTIGLTKTYDAASCEVSYRWICEMNAK
            ********** *** * *******.*****..*** *** ***
```

As used herein, the term "human DAP12" shall refer, when used in a protein context, to a protein having the primate amino acid sequence of SEQ ID NO: 2. The present invention also encompasses proteins comprising a substantial fragment thereof, e.g., mutants and polymorphic variants, along with a human derived polypeptide which exhibits the same biological function or interacts with human DAP12 specific binding components. These binding components typically bind to a human DAP12 with high affinity, e.g., at least about 100 nM, usually better than about 30 nM, preferably better than about 10 nM, and more preferably at better than about 3 nM. Homologous proteins are found in species other than humans, e.g., primates. While most of the description below is directed to DAP12, similar methods and features may be analogously applicable to the DAP10 and MDL-1 genes. Many limitations directed to DAP12 will correspond to terms in reference to DAP10 and MDL-1, though specific limitations relevant to one gene, e.g. a length limitation, will not necessarily intended to apply to the others.

The term "polypeptide" as used herein includes a fragment or segment, and encompasses a stretch of amino acid residues of at least about 8 amino acids, generally at least 10 amino acids, more generally at least 12 amino acids, often at least 14 amino acids, more often at least 16 amino acids, typically at least about 18 amino acids, more typically at least about 20 amino acids, usually at least about 22 amino acids, more usually at least about 24 amino acids, preferably at least about 26 amino acids, more preferably at least about 28 amino acids, and, in particularly preferred embodiments, at least about 30 or more amino acids, e.g., 33, 37, 41, 45, 49, 53, 57, 75, 100, 125, etc. In preferred embodiments, there will be a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

The term "binding composition" refers to molecules that bind with specificity to DAP12, DAP10, or MDL-I, e.g., in an antibody-antigen type fashion. Other interactions include, e.g., receptor component-receptor component, to form a receptor complex. Other members of the complex are likely to be the KIR, LIR, MIR, ILT, and CD94 forms described above. Another interesting interaction includes such a receptor complex with its counter-receptor, which itself may be a single protein or complex. For instance, the receptor for the KIR-DAP12 complex will probably be MHC Class I. Such interactions will typically be a protein—protein interaction, either covalent or non-covalent. The molecule may be a polymer, or chemical reagent. A functional analog may be a form with structural modifications, or may be a wholly unrelated molecule which has a molecular shape which interacts with the appropriate surface binding determinants. The analogs may serve as agonists or antagonists, see, e.g., Goodman, et al. (eds. 1990) *Goodman & Gilman's: The Pharmacological Bases of Therapeutics* (8th ed.) Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions. Such proteins will be, e.g., soluble/short forms of the KIR, MIR, ILT, or CD94 proteins. Disruption of those complexes will typically block the signal function.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-([3-cholamidopropyl]-dimethylammonio)-1-propane sulfonate), or in a low enough detergent concentration to not disrupt the tertiary structure of the protein.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 103 S, more usually less than about 6 S, and, in particular embodiments, preferably less than about 4 S, and more preferably less than about 3 S.

III. Physical Variants

This invention also encompasses proteins or peptides having substantial amino acid sequence identity with the amino acid sequences, e.g., of the human DAP12. It provides, e.g., 1-fold, 2-fold, 3-fold, 5-fold substitutions, preferably conservative. Such variants may be useful to produce specific antibodies, and often will share many or all biological properties.

Amino acid sequence identity is determined by optimizing residue matches. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Similar amino acid sequences are intended to include natural allelic variations in each respective protein sequence. Typical homologous proteins or peptides will have from 85–100% identity (if gaps can be introduced), to 90–100% identity (if conservative substitutions are included) with the amino acid sequence, e.g., of the human DAP12. Identity measures will be at least about 85%, generally at least about 87%, often at least about 89%, typically at least about 91%, usually at least about 93%, more usually at least about 95%, preferably at least about 97%, and more preferably at least about 98%, and in particularly preferred embodiments, at least about 99% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated human DAP and MDL DNA can be readily modified by nucleotide substitutions, nucleotide deletions, nucleotide insertions, and inversions of nucleotide stretches. These modifications will result in novel DNA sequences which encode useful antigens, their derivatives, or proteins having similar or antagonist activity. These modified sequences can be used to produce mutant antigens or to enhance expression. Enhanced expression may involve gene amplification, increased transcription, increased translation, and other mechanisms. Such mutant DAP12 derivatives include predetermined or site-specific mutations of the respective protein or its fragments. "Mutant DAP12" encompasses a polypeptide otherwise sharing important features of the human DAP12 as set forth above, but having an amino acid sequence which differs from that of DAP12 as found in nature, whether by way of deletion. Substitution, or insertion. In particular, "site specific mutant DAP12" is defined as having homology with an antigen of SEQ ID NO: 2, and as sharing relevant biological activities with those antigens. Similar concepts apply to different DAP12 proteins, particularly those found in various other mammals. As stated before, it is emphasized that descriptions are generally meant to encompass additional DAP and MDL proteins, not limited solely to the primate embodiment specifically discussed.

Although site specific mutation sites are predetermined, mutants need not be site specific. Human DAP12, DAP10, or MDL-1 mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with, e.g., a DAP12 polypeptide, is a continuous protein molecule having sequences fused in a typical peptide linkage, typically made as a single translation product and exhibiting properties derived from each source peptide. A similar concept applies to heterologous nucleic acid sequences. Particularly interesting fusions will be the DAP12 with its receptor partner, as discussed above. Both protein embodiments, and nucleic acids encoding both receptor complex components will be valuable.

In addition, new constructs may be made from combining similar functional domains from other proteins. For example, partner-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of partner-binding specificities and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

In certain situations, a DAP12 with multiple ITAM repeats, or an ITIM substitution, may be useful. Moreover, intact receptor functions may be achieved by splitting the long form of the transmembrane receptor into two separate subunits which interact as does the DAP12 with its partner. Thus, an intact long form receptor might be replaced with the pair of a shortened receptor with a DAP12. Nucleic acid constructs with the combination may also be prepared. Likewise with DAP10, and ITIM repeats, or an ITAM substitution.

IV. Functional Variants

The blocking of physiological response to DAP12 or DAP10 antigens may result from the inhibition of binding of a partner to the DAP receptor complex, likely through competitive inhibition. Thus, in vitro assays of the present invention will often use isolated protein, membranes from cells expressing a recombinant DAP12, soluble fragments comprising partner binding segments of these antigens, or fragments attached to solid phase substrates. These assays will also allow for the diagnostic determination of the effects of either binding segment mutations and modifications, or binding partner mutations and modifications.

This invention also contemplates the use of competitive drug screening assays, e.g., where neutralizing antibodies to the antigen or antigen fragments compete with a test compound for binding to the protein. In this manner, the antibodies can be used to detect the presence of a polypeptide which shares one or more binding sites of the antigen and can also be used to occupy binding sites on the protein that might otherwise be occupied by a binding partner. The invention also contemplates screening for compounds which interrupt the bridging of the charged residues in the transmembrane segments between partners.

Additionally, neutralizing antibodies against the DAP or MDL and soluble fragments of the DAP or MDL which contain a high affinity counterpart binding site, can be used to inhibit binding function in tissues, e.g., tissues experiencing abnormal physiology. Intracellular domain interactions with other components will also be targets for drug screening.

"Derivatives" of the DAP or MDL antigens include amino acid sequence mutants, glycosylation variants, and covalent or aggregate conjugates with other chemical moieties. Covalent derivatives can be prepared by linkage of functionalities to groups which are found in the DAP or MDL antigen amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. While there are no natural N-linked sites on the protein, there may be O-linked sites, or variants with such sites may be produced. Particularly preferred means for accomplishing this are by exposing the polypeptide to glycosylating enzymes derived from cells which normally provide such processing, e.g., human glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of, e.g., the DAP12 antigens or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the DAP12 antigens and other homologous or heterologous proteins are also provided. Homologous polypeptides may be fusions between different surface markers, resulting in, for instance, a hybrid protein exhibiting binding specificity of one or more marker proteins. Likewise, heterologous fusions may be constructed which would exhibit a combination of properties or activities of the derivative proteins. Typical examples are fusions of a reporter polypeptide, e.g., luciferase, with a segment or domain of an antigen, e.g., a partner-binding segment, so that the presence or location of a desired partner may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity reagents.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.) Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford.

This invention also contemplates the use of derivatives of the DAP12 antigens other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of binding partners. For example, a DAP12 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-DAP12 antibodies or its binding partners. The DAP12 antigens can also be labeled with a detectable group, for example radioiodinated onto a tyrosine, e.g., incorporated into the natural sequence, by the chloramine T procedure, covalently bound to rare earth chelates, or conjugated to another fluorescent moiety for use in diagnostic assays.

A solubilized DAP or MDL antigen of this invention can be used as an immunogen for the production of antisera or antibodies specific for the antigen or many fragments thereof. The purified antigens can be used to screen monoclonal antibodies or antigen-binding fragments prepared by immunization with various forms of impure preparations containing the protein. In particular, the term antibodies also encompasses antigen binding fragments of natural antibodies. The purified DAP or MDL can also be used as a reagent to detect antibodies generated in response to the presence of elevated levels of DAP, MDL, or cell fragments containing the antigen, both of which may be diagnostic of an abnormal or specific physiological or disease condition. Additionally, DAP or MDL fragments may also serve as immunogens to produce the antibodies of the present invention, as described immediately below. For example, this invention contemplates antibodies raised against amino acid sequences of, or encoded by nucleotide sequences of SEQ ID NO: 2, 6, 10, 12, or 14 or fragments thereof. In particular, this invention contemplates antibodies having binding affinity to or being raised against specific fragments which are predicted to lie outside of the lipid bilayer, either extracellular or Intracellular domains. Additionally, various constructs may be produced from fusion of a membrane associating segment to the otherwise extracellular exposed portion of the molecule. Other antigenic complexes may be used, including complexes of the DAP or MDL with a receptor partner.

The present invention contemplates the isolation of additional closely related variants. It is highly likely that allelic variations exist in different individuals exhibiting, e.g., better than 90–97% identity to the embodiment described herein.

The invention also provides means to isolate a group of related antigens displaying both distinctness and similarities in structure, expression, and function. Elucidation of many of the physiological effects of the antigens will be greatly accelerated by the isolation and characterization of distinct species counterparts of the antigens. In particular, the present invention provides useful probes for identifying additional homologous genetic entities in different species.

The isolated genes will allow transformation of cells lacking expression of DAP or MDL, e.g., either species types or cells which lack corresponding antigens and exhibit negative background activity. Various cell types, e.g., Jurkat, YT, or BAF3, transfected with CD94 or NKAT5 may exhibit signaling when transfected also with DAP12. Expression of transformed genes will allow isolation of antigenically pure cell lines, with defined or single specie variants. This approach will allow for more sensitive detection and discrimination of the physiological effects of signaling. Subcellular fragments, e.g., cytoplasts or membrane fragments, can be isolated and used.

Dissection of the critical structural elements which effect the various differentiation functions provided by receptor binding is possible using standard techniques of modern molecular biology, particularly in comparing members of the related class. See, e.g., the homolog-scanning mutagenesis technique described in Cunningham, et al. (1989) Science 243:1339–1336; and approaches used in O'Dowd, et al. (1988) J. Biol. Chem. 263:15985–15992; and Lechleiter, et al. (1990) EMBO J. 9:4381–4390.

In particular, receptor partner binding segments can be substituted between species variants to determine what structural features are important in both binding affinity and specificity. An array of different, e.g., DAP12 variants, will be used to screen for partners exhibiting combined properties of interaction with different species variants.

Intracellular functions would probably involve segments of the antigen which are normally accessible to the cytosol. However, antigen internalization may occur under certain circumstances, and interaction between intracellular components and the designated "extracellular" segments may occur. The specific segments of interaction of DAP12 with other intracellular components may be identified by mutagenesis or direct biochemical means, e.g., cross-linking, affinity, or genetic methods. Structural analysis by crystallographic or other physical methods will also be applicable. Further investigation of the mechanism of signal transduction will include study of associated components which may be isolatable by affinity methods.

Further study of the expression and control of DAP12 antigens will be pursued. The controlling elements associated with the antigens may exhibit differential developmental, tissue specific, or other expression patterns. Upstream or downstream genetic regions, e.g., control elements, are of interest.

Structural studies of the DAP12 antigens will lead to design of new variants, particularly analogs exhibiting agonist or antagonist properties. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Although the foregoing description has focused primarily upon the human DAP12, those of skill in the art will immediately recognize that the invention encompasses other DAP12 antigens, e.g., primate and other mammalian species variants. In addition, the DAP10 gene exhibits many features similar to DAP12, and will be modifiable in similar fashion. There is evidence that the DAP12, DAP10, and MDL-1 may associate with one another, and may all be associated into one multiprotein complex in certain circumstances.

V. Antibodies

Antibodies can be raised to the various allelic or species variants of DAP or MDL antigens and fragments thereof, both in their naturally occurring forms and in their recombinant forms. Additionally, antibodies can be raised to DAP12 in either their active forms or in their inactive forms, or native or denatured forms. Anti-idiotypic antibodies are also contemplated.

Antibodies, including binding fragments and single chain versions, against predetermined fragments of DAP or MDL can be raised by immunization of animals with conjugates of the fragments with immunogenic proteins. Monoclonal antibodies are prepared from cells secreting the desired antibody. These antibodies can be screened for binding to normal or defective DAP or MDL, or screened for agonistic or antagonistic functional activity. These monoclonal antibodies will usually bind with at least a $K_D$ of better than about 1 mM, more usually better than about 300 μM, typically better than about 10 μM, more typically better than about 30 μM, preferably better than about 10 μM, and more preferably better than about 3 μM, e.g., 1 μM, 300 nM, 100 nM, 30 nM, 10 nM, 3 nM, 1 nM, 300 pM, 100 pM, 30 pM, etc.

The antibodies, including antigen binding fragments, of this invention can have significant diagnostic or therapeutic value. They can be potent antagonists that bind to DAP12, DAP10, of MDL-1, and/or inhibit partner binding or inhibit the ability to elicit a biological response. They also can be useful as non-neutralizing antibodies and can be coupled to toxins or radionuclides so that when the antibody binds to the antigen, the cell itself is killed. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the DAP or MDL without inhibiting partner binding and/or signaling. As neutralizing antibodies, they can be useful in competitive binding assays. They will also be useful in detecting or quantifying DAP or MDL or its partners.

DAP12 fragments may be joined to other materials, particularly polypeptides, as fused or covalently joined polypeptides to be used as immunogens. A DAP12 and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated. Alternatively, cells may be collected for producing hybridomas.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345, 4,277, 437; 4,275,149; and 4,366,241. Also, recombinant immunoglobulins may be produced, see Cabilly, U.S. Pat. No. 4,816,567.

The antibodies of this invention can also be used for affinity chromatography in isolating the protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified DAP12 protein will be released.

The antibodies may also be used to screen expression libraries for particular expression products. Usually the antibodies used in such a procedure will be labeled with a moiety allowing easy detection of presence of antigen by antibody binding.

Antibodies raised against a DAP12, DAP10, or MDL-1 antigen will also be used to raise anti-idiotypic antibodies. These will be useful in detecting or diagnosing various immunological conditions related to expression of the respective antigens.

A DAP12 protein that specifically binds to or that is specifically immunoreactive with an antibody generated against a defined immunogen, such as an immunogen consisting of the amino acid sequence of SEQ ID NO: 2 or 6, is typically determined in an immunoassay. The immunoassay typically uses a polyclonal antiserum which was raised, e.g., to a protein of SEQ ID NO: 2 or 6. This antiserim is selected to have low crossreactivity against other CD3 family members, e.g., CD3 or FcεRγ, preferably from the same species, and any such crossreactivity is removed by immunoabsorption prior to use in the immunoassay.

In order to produce antisera for use in an immunoassay, the protein of SEQ ID NO: 2 or 6, or a combination thereof, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other CD3 family members, e.g., primate or rodent CD3, using a competitive binding immunoassay such as the one described in Harlow and Lane, supra, at pages 570–573. Preferably at least two CD3 family members are used in this determination in conjunction with either or some of the primate or rodent DAP12. These DAP12 family members can be produced as recombinant proteins and isolated using standard molecular biology and protein chemistry techniques as described herein. Similar techniques may be applied to the DAP10 or MDL-1.

Immunoassays in the competitive binding format can be used for the crossreactivity determinations. For example, the proteins of SEQ ID NO: 2 and/or 6 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2 and/or 6. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the DAP12 like protein of SEQ ID NO: 2 and/or 6). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

VI. Nucleic Acids

The human DAP or MDL probe, or fragments thereof, will be used to identify or isolate nucleic acids encoding homologous proteins from other species, or other related proteins in the same or another species. Hybridization or PCR technology may be used.

This invention contemplates use of isolated DNA or fragments to encode, e.g., a biologically active corresponding DAP12 polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact DAP12, or fragment, and have an amino acid sequence encoded by a nucleic acid of SEQ ID NO: 1 or 5. Further, this invention covers the use of isolated or recombinant DNA, or fragments thereof, which encodes a protein which is homologous to a DAP12 or which was isolated using cDNA encoding human DAP12 as a PCR or hybridization probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The invention embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity. Alternatively a mixture of purified sequences may be mixed, e.g., in a degenerate PCR approach.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with such an unnaturally occurring vector is encompassed, as are nucleic acids comprising sequence derived using a synthetic oligonucleotide process. Such is often done to replace a codon with a redundant codon encoding the same or a conservative amino acid, while typically introducing or removing, e.g., a restriction or sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode similar polypeptides to fragments of these antigens, and fusions of sequences from various different species variants.

A "fragment" in a nucleic acid context is a contiguous segment of at least about 17 nucleotides, generally at least 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 75, 100, 150, 200, 250, 300, etc.

A DNA which codes for, e.g., a DAP12 protein, will be particularly useful to identify genes, mRNA, and cDNA species which code for related or homologous antigens, as well as DNAs which code for homologous proteins from different species. Various DAP12 proteins should be similar in sequence and are encompassed herein. However, even proteins that have a more distant evolutionary relationship to the DAP12 can readily be isolated using these sequences if they exhibit sufficient similarity. Primate DAP12, DAP10, and MDL-1 proteins are of particular interest.

This invention further encompasses recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199. Operable association of heterologous promoters with natural gene sequences is also provided, as are vectors encoding, e.g., the DAP12 with a receptor partner.

Homologous nucleic acid sequences, when compared, exhibit significant sequence similarity. The standards for homology in nucleic acids are either measures for homology generally used in the art by sequence comparison or based upon hybridization conditions. The hybridization conditions are described in greater detail below.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981). *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:wwww.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Substantial identity in the nucleic acid sequence comparison context means either that the segments, or their complementary strands, when compared, are identical when optimally aligned, with appropriate nucleotide insertions or deletions. In at least about 50% of the nucleotides, generally at least about 56%, more generally at least about 59%, ordinarily at least about 62%, mom ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial identity exists when the segments will hybridize under selective hybridization conditions, to a strand, or its complement, typically using a sequence of SEQ ID NO: 1 or 5. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 125, 150, 200, 250, 300, etc.

Stringent conditions, in referring to identity in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 350 mM, more usually less than about 200 mM, typically less than about 150 mM, preferably less than about 100 mM, and more preferably less than about 50 mM. However, the combination of parameters is much more important than the measure of any single parameter. See, e.g., Wetmur and Davidson (1968) *J. Mol. Biol.* 31:349–370. Hybridization under stringent conditions should give a background of at least 2-fold over background, preferably at least 3–5 or more.

DAP or MDL from other human subjects can be cloned and isolated by hybridization or PCR. Alternatively, preparation of an antibody preparation which exhibits less allelic specificity may be useful in expression cloning approaches. Allelic variants may be characterized using, e.g., a combination of redundant PCR and sequence analysis, e.g., using defined primers, thereby providing information on allelic variation in a human population.

VII. Making DAP or MDL; Mimetics

DNA which encodes the DAP or MDL antigen or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length antigen or fragments which can in turn, e.g., be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, e.g., those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes, e.g., a human DAP12 antigen, or a fragment thereof encoding a biologically active polypeptide. The DNA can be under the control of a viral promoter and can encode a selection marker. This invention further contemplates use of such expression vectors which are capable of expressing eukaryotic cDNA coding for a primate DAP12 antigen in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of the human DAP12 gene or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988)(eds.) *Vectors: A Survey of Molecular Cloning Vectors and Their Uses*, Buttersworth, Boston, Mass.

Transformed cells are cells, preferably mammalian, that have been transformed or transfected with human DAP12 vectors constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include, e.g., prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express, e.g., the human DAP12 antigens or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236.

Lower eukaryotes, e.g., yeasts and Dictyostelium, may be transformed with, e.g., human DAP12 antigen sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series). Higher eukaryotic tissue culture cells are the preferred host cells for expression of the functionally active human DAP or MDL antigen protein. In principle, many higher eukaryotic tissue culture cell lines are workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express a human DAP or MDL antigen polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the DAP12 antigen gene may be co-transformed with one or more genes encoding mammalian or other glycosylating enzymes. Using this approach, certain mammalian glycosylation patterns will be achievable or approximated in prokaryote or other cells.

The DAP antigens might also be produced in a form which is phosphatidyl inositol (PI) linked, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283. Alternatively, purification segments may be engineered into the sequence, e.g., at the N-terminus or C-terminus, to assist in the purification or detection of the protein product. Means to remove such segments may also be engineered, e.g., protease cleavage sites.

Now that the entire sequences are known, the primate DAP or MDL antigens, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The human DAP or MDL antigens, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group.

Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156.

The prepared antigen and fragments thereof can be isolated and purified from the reaction mixture by means of peptide separation, for example, by extraction, precipitation, electrophoresis and various forms of chromatography, and the like. The human DAP12 antigens of this invention can be obtained in varying degrees of purity depending upon its desired use. Purification can be accomplished by use of the protein purification techniques disclosed herein or by the use of the antibodies herein described, e.g., in immunoabsorbent affinity chromatography. This immunoabsorbent affinity chromatography is carried out, e.g., by first linking the antibodies to a solid support and then contacting the linked antibodies with solubilized lysates of cells, lysates of other cells expressing, e.g., the DAP12 antigens, or lysates or supernatants of cells producing the DAP12 antigens as a result of DNA techniques, see below.

VIII. Uses

The present invention provides reagents which will find use in diagnostic applications as described elsewhere herein, e.g., in the general description for developmental or physiological abnormalities, or below in the description of kits for diagnosis.

Many of the receptors important in the activation of leukocytes (including the T cell antigen receptor, and immunoglobulin and Fc receptors) lack intrinsic signaling properties, but transmit their signals by coupling non-covalently with other membrane proteins that contain immunoreceptor tyrosine-based activation motifs (ITAM, YxxL-6 to 8 amino acid spacer-YxxL) in their cytoplasmic domains. For example, the T cell antigen receptor is associated with the CD3 gamma, delta, epsilon, and zeta proteins that contain ITAM sequences. Similarly, surface immunoglobulin on B cells is associated with CD79A and CD79B that contain ITAM and are required for signal transduction. The Fc receptors for IgG (CD16) on NK cells associates with CD3 zeta or the IgE Fc receptor-gamma subunit (both containing ITAM) and the high affinity IgE receptor on mast cells associated with the IgE Fc receptor-gamma subunit. Therefore, associated proteins containing ITAM represent a general strategy in the assembly of activating receptors on leukocytes.

Recently, several new families of leukocyte receptors have been identified that are structurally diverse. Certain isoforms of the KIR, ILT/MIR, Ly49, and CD94/NKG2 family of receptors have been implicated in positive signaling; however, these molecules (e.g. KIR-NKAT5, KIR-c139, ILT1, gp91/PIR, and CD94) lack sequences in their cytoplasmic domains that would be consistent with positive signaling capability.

Given that T cell antigen receptors, immunoglobulin receptors, and Fc receptors all achieve signaling function by association with another small subunit containing ITAM, it is likely that these other leukocyte receptors might use a similar strategy.

Therefore, available sequence databases were searched with protein sequences of human and mouse CD3 gamma, delta, epsilon, and zeta, and IgE Fc receptor-gamma chain. An EST designated LVA03A was identified that encodes a putative membrane protein of 12 kd with an acidic residue (D) in the transmembrane segment and a perfect ITAM sequence ~in the cytoplasmic domain. Cysteine residues in the short extracellular domain suggest the molecule might be expressed as a disulfide-bonded dimer. Distribution studies indicate the gene is transcribed in macrophages, dendritic cells, some T cells, and NK cells. This protein has been designated DNAX Activating Protein 12 (DAP12). An analogous gene was also identified, designated DAP10, which possesses ITIM motifs.

Receptors containing ITAM have all been important in inducing leukocyte function (e.g., T cell antigen receptor, immunoglobulin receptor, Fc receptor). Therefore, it is probably that DAP12 will have an important role in signal transduction in leukocytes. Agonists and antagonists of DAP12 should provide useful in either potentiating or inhibiting immune responses (i.e., proliferation, cytokine production, inducing apoptosis, or triggering cell-mediated cytotoxicity), respectively.

Receptors containing the YxxM motif have been identified as important in certain signaling molecules, e.g., CD28, CTLA-4, and CD19. Therefore, it is probably that DAP10 will have an important role in signal transduction. Agonists and antagonists of DAP10 should provide useful in either potentiating or inhibiting immune responses (i.e., proliferation, cytokine production, inducing apoptosis, or triggering cell-mediated cytotoxicity), respectively.

It is anticipated that DAP12 may non-covalently associate with several different membrane receptors, for example, but not necessarily limited to T cell antigen receptor, the pre-T cell antigen receptor, the immunoglobulin receptor, Fc receptors, the KIR family of receptors, the ILT/MIR family of receptors, the LAIR family of receptors, the gp91/PIR family of receptors, the Ly49 family of receptors (specifically Ly49D and Ly49H), and the CD94/NKG2 family of receptors. Among these is the MDL-1. Therefore, reagents to affect DAP12 interaction with said receptors may either enhance or suppress the function of these molecules for therapeutic intervention (i.e., augment immunity for vaccination or immunodeficiency diseases or suppress immune responses in the case of autoimmune diseases or transplantation). Combinations of DAP with any one of these receptors will be useful, e.g., for drug screening for interrupters of the interaction and subsequent signaling, as will antibodies to the structural complexes arising form their interaction.

The DAP12 may be playing a role in Beta2 like integrin signaling. It is clear that Beta2 integrin can transmit a P Tyr kinase dependent signal involving Syk. In Syk knockouts, Beta2 does not signal. The pathway also probably involves FcγR (in Monocytes/Macrophages and B cells) as a negative regulator. However, there is no known way for Syk to associate with Beta2 integrins as they have no ITAM containing sequences in there cytoplasmic domains. Moreover, there is no evidence that the known ITAM containing proteins can associate with Beta2. Thus, DAP12 would be a prime candidate or prototype for one that would associate with Beta2.

This invention also provides reagents with significant therapeutic value. The human DAP12 or DAP10 (naturally occurring or recombinant), fragments thereof and antibodies thereto, along with compounds identified as having binding affinity to primate DAP, should be useful in the treatment of conditions associated with abnormal B cell response, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal triggering of DAP12 should be a likely target for an agonist or antagonist of the antigen. DAP12 likely plays a role in activation or regulation of immune cells, which affect immunological responses, e.g., autoimmune disorders or allergic responses.

In addition, the DAP:DAP binding partner interaction may be involved in T, NK, DC, or monocyte cell interactions that permit the activation, proliferation, and/or differentiation interacting cells. If so, treatment may result from interference with the DAP:DAP binding partner signal transduction, particularly potentiating or inhibiting immune responses such as proliferation, cytokine production, inducing apoptosis, or triggering cell-mediated cytotoxicity. Blocking of the signal may be effected, e.g., by soluble DAP or antibodies to DAP, or drugs which disrupt the functional interaction of the DAP with its receptor complex partner.

Other abnormal developmental conditions are known in each of the cell types shown to possess DAP12 or DAP10 mRNA by Northern blot analysis, e.g., lymphocytes, NK, monocytes, and dendritic cells. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. For example, therapeutic immunosuppression may be achieved by blocking T lymphocyte and B lymphocyte interaction through this molecule. It will represent an important therapy for controlling autoimmune diseases and graft rejection during transplantation. The blockage may be effected with blocking binding compositions, e.g., neutralizing antibodies.

Recombinant DAP or DAP antibodies can be purified and then administered to a patient. These reagents can be combined for therapeutic use with additional active ingredients, e.g., in conventional pharmaceutically acceptable carriers or diluents, e.g., immunogenic adjuvants, along with physiologically innocuous stabilizers and excipients. These combinations, and compositions provided, can be sterile filtered and placed into dosage forms as by lyophilization in dosage vials or storage in stabilized aqueous preparations. This invention also contemplates use of antibodies or binding fragments thereof which are not complement binding.

Drug screening using DAP or fragments thereof can be performed to identify compounds having binding affinity to a DAP, including isolation of associated components. Subsequent biological assays can then be utilized to determine whether the compound has intrinsic stimulating activity and is therefore a blocker or antagonist in that it blocks signaling. Likewise, a compound having intrinsic stimulating activity can activate the antigen and is thus an agonist in that it simulates the activity of a DAP. This invention further contemplates the therapeutic use of antibodies to DAP as antagonists. This approach should be particularly useful with other DAP or MDL species variants. The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Human DAP or MDL, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for topical, oral, rectal, nasal, or parenteral (including subcutaneous, intramuscular, intravenous and intradermal) administration. The formulations may conveniently be presented in unit dosage form, in sterile forms, or may be prepared by many methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. The therapy of this invention may be combined with or used in association with other agents.

Both the naturally occurring and the recombinant forms of the DAP or MDL antigens of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble DAP or MDL as provided by this invention.

For example, antagonists can normally be found once a DAP or MDL has been structurally defined. Testing of potential antagonists is now possible upon the development of highly automated assay methods using a purified DAP or MDL. In particular, new agonists and antagonists will be discovered by using screening techniques made available herein. Of particular importance are compounds found to have a combined binding affinity for multiple DAP12, DAP10, or MDL-1 proteins, e.g., compounds which can serve as antagonists for allelic variants of DAP or MDL.

Moreover, since the signaling through the DAP:DAP binding partner may function in combination with other signals, combination therapy with such pathways will also be considered. Thus, antagonism of multiple signal pathways, or stimulation with multiple pathways may be useful. Moreover, with the association of the DAP12 with MDL-1, and possibly also with DAP10, various combinations of the described genes may be important.

This invention is particularly useful for screening compounds by using the recombinant antigens in any of a variety of drug screening techniques. The advantages of using a recombinant protein in screening for specific compounds include: (a) improved renewable source of the DAP12 from a specific source; (b) potentially greater number of antigen molecules per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing the DAP and/or MDL. Cells may be isolated which express a DAP in isolation from others, or in combination with its receptor complex partner. Such cells, either in viable or fixed form, can be used for standard antigen/partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of DAP) are contacted and incubated with a labeled compound having known binding affinity to the antigen, and a test compound whose binding affinity to the DAP is being measured. The bound compound and free compound are then separated to assess the degree of binding. The amount of test compound bound is inversely proportional to the amount of labeled compound binding measured. Many techniques can be used to separate bound from free compound to assess the degree of binding. This separation step could typically involve a procedure such as adhesion to filters followed by washing, adhesion to plastic followed by washing, or centrifugation of the cell membranes. Viable cells could also be used to screen for the effects of drugs on DAP mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the human DAP or MDL. These cells are stably transformed with DNA vectors directing the expression of human DAP or MDL antigen. Essentially, the membranes would be prepared from the cells and used in a receptor complex binding assay such as the competitive assay set forth above.

Still another approach is to use solubilized, unpurified or solubilized, purified DAP from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to human DAP or MDL and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified DAP, and washed. The next step involves detecting bound DAP.

Rational drug design may also be based upon structural studies of the molecular shapes of the DAP or MDL and other effectors. Effectors may be other proteins which mediate other functions in response to receptor complex binding, or other proteins which normally interact with the antigen. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified DAP or MDL can be coated directly onto plates for use in the aforementioned drug screening techniques. However, non-neutralizing antibodies to these antigens can be used as capture antibodies to immobilize the respective DAP or MDL on the solid phase.

IX. Kits

This invention also contemplates use of DAP or MDL proteins, fragments thereof, peptides, and their fusion products in a variety of diagnostic kits and methods for detecting the presence of DAP or MDL, or a binding partner. Typically the kit will have a compartment containing either a defined DAP or MDL peptide or gene segment or a reagent which recognizes one or the other.

A kit for determining the binding affinity of a test compound to, e.g., a DAP12, would typically comprise a test compound; a labeled compound, for example a receptor complex binding partner or antibody having known binding affinity for the DAP12; a source of DAP12 (naturally occurring or recombinant); and a means for separating bound from free labeled compound, such as a solid phase for immobilizing the DAP12. Once compounds are screened, those having suitable binding affinity to the DAP12 can be evaluated in suitable biological assays, as are well known in the art, to determine whether they act as agonists or antagonists. The availability of recombinant DAP12 polypeptides also provide well defined standards for calibrating such assays.

A preferred kit for determining the concentration of, e.g., a DAP12, in a sample would typically comprise a labeled compound, e.g., antibody, having known binding affinity for the DAP12, a source of DAP12 (naturally occurring or recombinant) and a means for separating the bound from free labeled compound, e.g., a solid phase for immobilizing the DAP12. Compartments containing reagents, and instructions, will normally be provided.

One method for determining the concentration of DAP12 in a sample would typically comprise the steps of: (1) preparing membranes from a sample comprised of a DAP12 source; (2) washing the membranes and suspending them in a buffer; (3) solubilizing the DAP12 by incubating the membranes in a culture medium to which a suitable detergent has been added; (4) adjusting the detergent concentration of the solubilized DAP12; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for human DAP or DAP fragments are useful in diagnostic applications, e.g., to detect the presence of elevated levels of DAP and/or its fragments. Such diagnostic assays can employ lysates, live cells, fixed cells, immunofluorescence, cell cultures, body fluids, and further can involve the detection of antigens related to the DAP in serum, or the like. Diagnostic assays may be homogeneous (without a separation step between free reagent and antigen-partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a DAP or to a particular fragment thereof. These assays have also been extensively discussed in the literature. See, e.g., Harlow and Lane (1988) *Antibodies: A Laboratory Manual*, CSH.

Anti-idiotypic antibodies may have similar use to diagnose presence of antibodies against a human DAP, as such may be diagnostic of various abnormal states. For example, overproduction of DAP may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled DAP or MDL is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the test compound, DAP, MDL, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free binding compound, or alternatively the bound from the free test compound. The DAP or MDL can be immobilized on various matrices followed by washing. Suitable matrices include plastic such as an ELISA plate, filters, and beads. Methods of immobilizing the DAP or MDL to a matrix include, without limitation, direct adhesion to plastic, use of a capture antibody, chemical coupling, and biotin-avidin. The last step in this approach involves the precipitation of antigen/binding compound complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

The methods for linking proteins or their fragments to the various labels have been extensively reported in the literature. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of polynucleotide or oligonucleotide sequences taken from the sequence of a DAP or MDL. These sequences can be used as probes for detecting levels of the antigen in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Receptor Complex Partner

The description of the DAP and MDL proteins herein provide means to identify receptor complex partners. Such receptor complex partner should bind specifically to the DAP12, DAP10, and/or MDL-1 with reasonably high affinity. Various constructs are made available which allow either labeling of the DAP or MDL to detect its partner. For example, directly labeling DAP12, fusing onto it markers for secondary labeling, e.g., FLAG or other epitope tags, Ig domain fusions, etc., will allow detection of binding partners. This can be histological, as an affinity method for biochemical purification, or labeling or selection in an expression cloning approach. A two-hybrid selection system may also be applied making appropriate constructs with the available DAP12 sequences. See, e.g., Fields and Song (1989) *Nature* 340:245–246.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Computer sequence analysis is performed, e.g., using available software programs, including those from the GCG (U. Wisconsin) and GenBank sources. Public sequence databases were also used, e.g., from GenBank and others.

II Amplification of Human DAP Fragment by PCR

Two primers are designed according to the provided sequences. To increase the chances of obtaining PCR products, human THP-1 cells, Th1 T cells, monocytes activated with LPS, IFN-γ and IL-10, or NK cells are used. A product is purified, subcloned into pCR™ vector (Invitrogen, San Diego, Calif.), and then sequenced. See SEQ IS NO: 1, 2, 5, 6, 7, 8, 9, 10, 11, 12, 13, and 14.

III. Tissue Distribution of Human DAP and MDL

Hybridization analysis or PCR analysis can be used. Preliminary data by hybridization suggests expression in macrophages, dendritic cells, some T cells, and NK cells. Analysis may be by Northern, Southern, or cDNA Northern techniques. Western blotting may be performed using appropriate antibodies or serum. Genomic sequences can also be determined by standard techniques.

Southern blot analysis of human genomic DNA revealed a restriction enzyme digest pattern consistent with the genomic organization of a single DAP12 gene. Northern blot analysis indicated the abundant presence of ~0.7 kb DAP12 transcripts in peripheral blood leukocytes and spleen human, but not in thymus, prostate, testis, ovary, small intestine or colon. DAP12 transcripts were detect in RNA isolated from two human NK cell lines NKL and NK92, but not in the Jurkat T leukemia cell line or the JY EBV-transformed B lymphoblastoid cell line. Southern blot analysis of a large panel of cDNA libraries revealed predominant expression of DAP12 in resting human peripheral blood mononuclear cells, dendritic cells (from which DAP12 was cloned), peripheral blood monocytes, and NK cell lines and clones.

Initial distribution data on DAP10 indicates that it is highly expressed in T cells, NK cells, monocytes, and dendritic cells. It does not appear to be highly expressed in EBV-transformed B cells.

The MDL-1 seems restricted in expression to monocytes, macrophages, and dendritic cells as analyzed by Southern blot analysis of a large panel of cDNA libraries and by RT-PCR. MDL-1 transcripts were not detected in T cells (pre-T cells, resting T cells, Th1 and Th2 T cell lines and clones), B cells, NK cells, granulocytes, mast cell lines, and endothelial cell lines. A panel of human fetal tissue libraries displayed hybridization with the fetal spleen library but with no other library, suggesting that the MDL-1 transcript is not expressed in cell types of non-hematopoietic origin.

IV. Isolation of a Rodent DAP and MDL cDNA

SEQ ID NO: 5, 9, and 13 allow design of a probe of primer which allow isolation of mouse counterparts. With the primate and rodent sequences, other species counterparts can be identified using conserved sequences, either nucleic acid or epitopes.

V. Sequencing of Isolated Clone

Standard methods are used to sequence a clone isolated as described above. The appropriate constructs for expression are prepare, e.g., in a coli, baculovirus, or mammalian cell type. Preferred cell types include Jurkat, YT, or Baf3. See ATCC catalog.

VI. Expression of Human DAP and MDL Protein

Soluble DAP12-FLAG protein is transiently expressed in COS-7 cells. A recombinant form of DAP12 displaying the FLAG peptide at the amino or carboxy terminus (Hoppe, et al. (1988) Biotechnology 6:1205–1210) is introduced into the expression vector pME18S and subsequently transfected into COS-7 cells by electroporation. Electroporated cells are grown in DMEM medium supplemented either with 1% Nutridoma HU (Boehringer Mannheim, Mannheim, Germany) or DMEM medium alone. Similar methods are used for the DAP10 or MDL-1.

VII. Purification of Soluble DAP FLAG Protein

Supernatant containing soluble DAP12 FLAG is passed on a 20 ml column of $Cu^{++}$ ions attached to a Chelating Sepharose Fast Flow matrix (Pharmacia, Upsalla, Sweden). After washing with binding buffer (His-Bind Buffer kit, Novagen, Madison, Wis.), the proteins retained by the metal ions are eluted with a gradient of Imidazole. The content of human DAP12 FLAG in the eluted fractions is determined, e.g., by dot blot using the anti-FLAG monoclonal antibody M2 (Eastman Kodak, New Haven, Conn.) or by Coomassie blue and silver staining of reducing SDS-PAGE. The DAP12 FLAG protein containing fractions is then pooled and dialyzed against PBS.

VIII. Stable Expression of Membrane DAP or MDL

A native membrane form is subcloned into an expression vector, e.g., pMAMneo (Clontech, Palo Alto, Calif.), which contains the RSV-LTR enhancer linked to the dexamethasone-inducible MMTV-LTR promoter. This construct is then transfected into NIH-3T3 cells by electroporation. Transfected NIH-3T3 cells are seeded in selective 0.5 mg/ml Geneticin (G418; Boehringer-Mannheim, Mannheim, Germany) DMEM supplemented with 10% Fetal Calf Serum.

Biochemical characterization of membrane DAP12 protein in stable transfected NIH-3T3 cells may be performed with metabolic labeling. Cells are cultivated, e.g., in DMEM medium supplemented with 10% Fetal Calf Serum and 1 µM final dexamethasone (Sigma, Saint Quentin Fallavier, France). Cells are then incubated with $^{35}$S-Met and $^{35}$S-Cys to label cellular proteins. Analysis of the proteins under reducing conditions on SDS-PAGE should show a 12 kDa protein, but not in the lysate of untransfected NIH-3T3 cells. Certain other structural features are known, e.g., glycosylation sites, etc.

IX. Preparation of Antibodies Specific for DAP

Inbred Balb/c mice are immunized intraperitoneally with recombinant forms of the primate protein. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response.

Monoclonal antibodies may be made. For example, splenocytes are fused with an appropriate fusion partner and hybridomas are selected in growth medium by standard procedures. Hybridoma supernatants are screened for the presence of antibodies which bind to the human DAP12, e.g., by ELISA or other assay. Antibodies which specifically recognize human DAP12 but not species variants may also be selected or prepared.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156–4160; Barry, et al. (1994) *BioTechniques* 16:616–619; and Xiang, et al. (1995) *Immunity* 2: 129–135.

Antibodies have been made, and used, as described below, for both the DAP proteins.

X. Mapping of Human DAP

Chromosome spreads are prepared. In situ hybridization is performed on chromosome preparations obtained from phytohemagglutinin-stimulated human lymphocytes cultured for 72 h. 5-bromodeoxyuridine was added for the final seven hours of culture (60 µg/ml of medium), to ensure a posthybridization chromosomal banding of good quality.

A PCR fragment, amplified with the help of primers, is cloned into an appropriate vector. The vector is labeled by nick-translation with $^3$H. The radiolabeled probe is hybridized to metaphase spreads at final concentration of 200 ng/ml of hybridization solution as described in Mattei, et al. (1985) *Hum. Genet.* 69:327–331.

After coating with nuclear track emulsion (KODAK NTB$_2$), slides are exposed. To avoid any slipping of silver grains during the banding procedure, chromosome spreads are first stained with buffered Giemsa solution and metaphase photographed. R-banding is then performed by the fluorochrome-photolysis-Giemsa (FPG) method and metaphases re-photographed before analysis.

The genomic organization of human DAP12 consists of 5 exons spanning ~4 kb on chromosome 19q13.1. The human KIR genes (Baker, et al. (1995) *Chromosome Research* 3:511) and the related LAIR (Meyaard, et al. (1997) *Immunity* 7:283–290, and ILT/MIR (Wagtmann, et al. (1997) *Current Biology* 7:615–618) genes are all located nearby on chromosome 19q 13.4.

XI. DAP and MDL Biology

DAP12 is a disulfide-bonded homodimer, containing an immunoreceptor tyrosine-based activation motif (ITAM) in its cytoplasmic domain, that is predominantly expressed in NK cells, monocytes, and dendritic cells. This molecule non-covalently associates with membrane glycoproteins of the killer cell inhibitory receptor (KIR) family that lack immunoreceptor tyrosine-based inhibitory motifs (ITIM) in their cytoplasmic domain. Cross-linking KIR2DS2-DAP12 complexes expressed in transfectants results in cellular activation, as demonstrated by tyrosine-phosphorylation of cellular proteins and up-regulation of early activation antigens. Phosphorylated DAP12 peptides bind ZAP-70 and Syk protein tyrosine kinases, suggesting an activation pathway similar to the T and B cell antigen receptors.

NK cells express membrane receptors of the immunoglobulin and C-type lectin superfamilies that recognize MHC class I and inhibit NK cell-mediated cytotoxicity. Lanier (1997) *Immunity* 6:371–378. These inhibitory receptors (including human KIR, human CD94/NKG2A, and rodent Ly49) possess ITIM in their cytoplasmic domains that recruit SH2-domain containing protein tyrosine phosphatases (SHP) 1 or 2, resulting in inactivation of NK cell function. Burshtyn, et al. (1996) *Immunity* 4:77–85; Olcese, et al. (1996) *J. Immunol.* 156:4531–4534; and Houchins, et al. (1997) *J. Immunol.* 158:3603–3609. Certain isoforms of the KIR, Ly49, and CD94/NKG2 receptors lack ITIM sequences and it has been proposed that these 'non-inhibitory' receptors may activate, rather than inhibit, NK cell function. Houchins, et al. (1997) J. Immunol. 158:3603–3609; Biassoni, et al. (1996) *J. Exp. Med.* 183:645–650; and Mason, et al. (1996) *J. Exp. Med.* 184:2119–2128. When the non-inhibitory KIR2DS2 molecule was expressed by transfection in the RBL-2H3 basophilic leukemia no cellular activation was observed when the receptors were ligated, suggesting that these 'non-inhibitory' NK receptors may lack intrinsic signaling properties. Bléry, et al. (1997) *J. Biol. Chem.* 272:8989–8996.

Recently, Olcese, et al. (1997) *J. Immunol.* 158:5083–5086, reported that an unknown phosphoprotein of ~12 kD, expressed as a disulfide-bonded dimer, was co-immunoprecipitated with a non-inhibitory KIR2DS2 glycoprotein from NK cell lysates. Cell surface Ig receptors, T cell antigen receptors (TcR), and certain Fc receptors (FcR) non-covalently associate with small transmembrane proteins (e.g. CD3δ, γ, ε, ζ subunits, CD79α, β, FcεRI-γ) containing ITAM sequences (D/Exx YxxL/I-x$_{6-8}$-YxxL/I; Reth (1989) *Nature* 338:383–384) that are required for signal transduction by these receptor complexes. Chan, et al. (1994) *Ann. Rev. Immunol.* 12:555–592. Therefore, it seems likely that these non-inhibitory NK cell receptors might require an associated protein with similar properties to mediate positive signal transduction.

A database of expressed tag sequences (EST) from a large panel of cDNA libraries was searched with a TBLASTN algorithm program for molecules bearing homology with the human CD3δ, γ, ε, ζ and FcεRI-γ protein sequences. An EST from a human CD1+ dendritic cell library was selected for further study based on identification of an ITAM in this molecule. Sequencing of the 604 bp cDNA revealed an open reading frame of 339 nucleotides, encoding a putative type I membrane protein of 113 amino acids (see SEQ ID NO: 1 and 2). The protein, designated DAP12, is composed of a 27 aa leader, 14 aa extracellular domain, 24 aa transmembrane segment, and 48 aa cytoplasmic region. Although DAP12 has less than 25% homology with the human CD3δ, γ, ε, ζ and FcεRI-γ proteins, the cytoplasmic domain contains the peptide, ESPYQELQGQRSDVYSDL (see SEQ ID NO: 2), that precisely corresponds to the prototype ITAM consensus sequence. Potential sites for phosphorylation by protein kinase C (residues 79–81 and 107–109) and casein kinase II (residues 85–88) are also present in the DAP12 cytoplasmic region. The transmembrane region contains a charged amino acid (D), also conserved in the transmembrane domain of the CD3 subunits. A potential murine homolog of DAP12 is 70% homologous with the human DAP12 protein and has a conserved D residue in the transmembrane region, conserved C residues in the extracellular domain and an ITAM in the cytoplasmic region.

A conspicuous feature of the non-inhibitory KIR (Biassoni, et al. (1996) *J. Exp. Med.* 183:645–650), Ly49D and Ly49H (Mason, et al. (1996) *J. Exp. Med.* 184:2119–2128), CD94 (Chang, et al. (1995) *Eur. J. Immunol.* 25:2433–2437), NKG2C and NKG2E (Houchins, et al. (1991) *J. Exp. Med.* 173:1017–1020), and ILT1 (Samaridis and Colonna (1997) *Eur. J. Immunol.* 27:660–665) receptors is the presence of a basic amino acid (K or R) in the transmembrane domain. Given the precedent for interactions between proteins of multi-subunit receptor complexes via oppositely charged amino acids in the transmembrane domains, e.g. the CD3/TcR complex (Chan, et al. (1994) *Ann. Rev. Immunol.* 12:555–592), we examined whether DAP12 associates with the non-inhibitory KIR2DS2 glycoprotein containing a K in the transmembrane region (Colonna and Samaridis (1995) *Science* 268:405–408). The murine Ba/F3 pre-B cell line was transfected with a cDNA encoding KIR2DS2 either alone or together with a DAP12 cDNA containing a FLAG epitope tag at the N terminus to permit detection with an anti-FLAG mAb. Transfectants were selected by flow cytometry for cell surface expression based on positive staining with anti-KIR mAb DX27 or anti-anti-FLAG mAb M2. KIR2DS2 Ba/F3 and KIR2DS2+ DAP12-FLAG Ba/F3 transfectants were surface labeled with $^{125}$I, lysed in 1% digitonin to preserve non-covalent associations of membrane protein complexes, and immunoprecipitated with anti-KIR mAb or anti-FLAG mAb. The tyrosine residue in the FLAG epitope provided a site for radioiodination, permitting visualization of the DAP12 protein. Anti-KIR mAb immunoprecipitated an $^{125}$I labeled species of ~50–60 kD from both the KIR2DS2 Ba/F3 cells and KIR2DS2+DAP12-FLAG Ba/F3 transfectants, consistent with the predicted molecular weight of the KIR2DS2 glycoprotein. An additional $^{125}$I labeled protein of 12 kD was co-immunoprecipitated with anti-KIR mAb from the KIR2DS2+DAP12-FLAG transfectant, but not from the transfectant expressing only KIR2DS2. Reciprocally, an $^{125}$I labeled glycoprotein migrating identical to KIR2DS2 was co-immunoprecipitated with anti-FLAG mAb from the KIR2DS2+DAP12-FLAG Ba/F3 cells, but not from the KIR2DS2 only transfectant. Comparison of immunoprecipitates analyzed by SDS-PAGE using either reducing or non-reducing conditions indicate that DAP12 is expressed on the cell surface as a disulfide-bonded dimer. It should be noted that we were unable to detect cell surface expression of DAP12 on the surface of Ba/F3 cells transfected with the DAP12-FLAG cDNA alone, without KIR2DS2. However, DAP12-FLAG proteins were detected in the cytoplasm, suggesting that DAP12 may require association with its partner subunits for efficient transport to the cell surface, similar to the situation with the CD3 proteins (Clevers, et al. (1988) *Ann. Rev. Immunol.* 6:629–662). Additionally, preliminary results indicated that DAP12 does not associate with the inhibitory KIR isoforms that lack a charged residue in their transmembrane domain. A peptide corresponding to the cytoplasmic domain of DAP12 (ITETESPY*QELQGQRSDVY*SDLNTQRP; see SEQ ID NO: 2) was synthesized either as an unphosphorylated protein or containing phosphates on both Y residues. Lysates from Jurkat T cells or NK cell clone A6 were incubated with the biotinylated peptides and complexes precipitated using avidin-agarose. Western blot analysis demonstrated that a DAP12 peptide phosphorylated on both Y residues, but not the unphosphorylated peptide, formed complexes with the ZAP-70 kinase. The tyrosine phosphorylated DAP12 peptide, but not the unphosphorylated DAP12 peptide, also formed a complex with the Syk protein tyrosine kinase in lysates from NK cells. The binding of these kinases to phosphorylated DAP12 is remarkably reminiscent of the interactions that have been demonstrated between the phosphorylated ITAM-containing CD3 subunits and Syk or ZAP-70 kinases during TcR signaling. Iwashima, et al. (1994) *Science* 263:1136–1139; and Chan, et al. (1994) *J. Immunol.* 152:47584766.

Ligation of the CD3/TcR complex on T cells or the Ig receptor complex on B cells resulted in cellular activation. Therefore, studies were undertaken to examine the functional consequence of cross-linking the KIR2DS2-DAP12 complex. Ba/F3 transfectants expressing either KIR2DS2 alone or the KIR2DS2-DAP12-FLAG complex were incubated with anti-KIR mAb DX27 or anti-FLAG mAb, followed by a goat anti-mouse Ig to provide cross-linking. Examination of total cellular proteins in Ba/F3 cells expressing the KIR2DS2-DAP12-FLAG complex that were stimulated with anti-KIR or anti-FLAG mAb revealed tyrosine phosphorylation of several cellular substrates. Immunoprecipitation with anti-FLAG mAb and Western blot analysis with anti-phosphotyrosine mAb demonstrated that cross-linking the KIR2DS2-DAP12-FLAG transfectants with anti-KIR mAb induced tyrosine phosphorylation of the DAP12 protein and resulted in the association of phosphorylated DAP12 with the Syk protein tyrosine kinase. By contrast, Ba/F3 cells expressing only KIR2DS2 were not activated by cross-linking with anti-KIR mAb. Similarly, up-regulation of CD69 expression was observed in Jurkat T leukemia cells transfected with both KIR2DS2 and DAP12, but not KIR2DS2 alone, when these receptors were cross-linked with anti-KIR mAb. These results indicate that DAP12 is necessary and responsible for KIR2DS2 signal transduction in these host cells and are in accordance with prior observations demonstrating that KIR2DS2 molecules are functional in NK, cells, but not in transfectants expressing only KIR2DS2. Bléry, et al. (1997) *J. Biol. Chem.* 272:8989–8996.

These studies suggest that DAP12 may associate with the non-inhibitory isoforms of the KIR molecules in NK cells and permit cellular activation via these receptors, similar to the function of the CD3 subunits in the TcR complex and CD79 subunits in the B cell receptor complex. Expression of DAP12 in monocytes and dendritic cells predicts association with other receptors similar to the non-inhibitory KIR present in these cell types. Likely candidates are the recently identified ILT/MIR family of molecules expressed by human monocytes (Wagtmann, et al. (1997) *Current Biology* 7:615–618; and Samaridis and Colonna (1997) *Eur. J. Immunol.* 27:660–665) and the PIR-A molecules in rodent myeloid and B cells (Hayami, et al. (1997) *J. Biol. Chem.* 272:7320–7327; and Kubagawa, et al. (1997) *Proc. Natl. Acad. Sci. USA* 94:5261–5266). In addition, the physical properties of DAP12 are similar to a novel dimeric 12 kD phosphoprotein identified in the pre-T cell receptor complex on murine thymocytes. Takase, et al. (1997) J. Immunol. 159:741–747. Thus, DAP12 may function in cellular activation mediated by a diverse array of receptors in distinct cell lineages.

Cloning and Sequence Analysis

TBLASTN searches of the DNAX sequence database were made using the human CD3δ, γ, ε, ζ and FcεRI-γ protein sequences. The cDNA insert in plasmid LL603, identified in a human CD1+ dendritic cell library, was isolated and subjected to automated sequencing (ABI).

DNA and RNA

RNA from human tissues and human genomic DNA were purchased from Clontech (Palo Alto, Calif.). Northern and Southern blot analysis were performed as described. Chang, et al. (1995) *Eur. J. Immunol.* 25:2433–2437.

Transfection

A cDNA containing the CD8 leader segment, followed by the FLAG peptide epitope, and joined to the extracellular, transmembrane and cytoplasmic segments of DAP12 was subcloned into the pMX-puro retroviral vector (Onihsi, et al. (1996) *Exp. Hematology* 24:324–329; generously provided by Dr. T. Kitamura, DNAX), packaged using the Phoenix cell line (kindly provided by Dr. G. Nolan, Stanford), and virus was used to infect the mouse pre-B cell line Ba/F3 (Onihsi, et al. (1996) *Exp. Hematology* 24:324–329). The NKAT5 cDNA (Colonna and Samaridis (1995) *Science* 268:405–408) encoding KIR2DS2 (kindly provided by Dr. M. Colonna, Basel) was subcloned into the pMX-neo retroviral vector. Ba/F3 cells were infected, drug selected, and transfectants isolated using flow cytometry. Onihsi, et al. (1996) *Exp. Hematology* 24:324–329. DAP12 cDNA was subcloned into the pEF-BOS vector for transient expression in Jurkat cells using electroporation for introduction of the plasmid. Wu, et al. (1995) *Mol. Cell. Biol.* 15:4337–4346.

Immunoprecipitation.

Cells were labeled with $^{125}$I and solubilized in lysis buffer (pH 7.8, 1% digitonin (Sigma), 0.12% Triton-X100, 150 mM NaCl, 20 mM triethanolamine, 0.01% NaN$_3$, and protease inhibitors). Lanier, et al. (1989) *Nature* 342:803–805. Cell lysates were incubated on ice for 2 hr with Pansorbin (Calbiochem) coated with rabbit anti-mouse Ig (Sigma) and mouse anti-KIR2D mAb DX27, anti-FLAG mAb M2 (Kodak), or control IgG and then washed in Tris-buffered saline (TBS, 50 mM Tris, 150 mM NaCl, pH 8.0) containing 5 mM CHAPS (Sigma) and protease inhibitors. Lanier, et al. (1989) *Nature* 342:803–805. Biotinylated peptides corresponding to residues ITETESPY*QELQGQRSDVY*SDLNTQRP in the cytoplasmic domain of DAP12 (see SEQ ID NO: 2) were synthesized, either unphosphorylated or containing phosphate on both Y residues (generously provided by Dr. C. Turck, UCSF). Control unphosphorylated and Y-phosphorylated CD3ζ peptides (Iwashima, et al. (1994) *Science* 263:1136–1139) were a gift from Dr. A. Weiss (UCSF). Biotinylated peptides were incubated with lysates from Jurkat or NK clone A6 cells, precipitated with avidin-agarose, and washed in Tris-buffered saline (50 mM Tris, 150 mM NaCl, pH 7.8) containing 1% NP-40 and protease inhibitors (Iwashima, et al. (1994) *Science* 263:1136–1139). Immunoprecipitates were analyzed by Western blot (Phillips, et al. (1996) *Immunity* 5:163–172) using anti-ZAP-70 mAb or rabbit anti-Syk specific antiserum (Iwashima, et al. (1994) Science 263:1136–1139; kindly provided by Art Weiss, UCSF).

Cell Activation

Ba/F3 cells expressing either KIR2DS2 alone, DAP12 (FLAG epitope tagged) alone, or the KIR2DS2-DAP12 complex were incubated with the indicated mAbs at 4° C., washed, and then cross-linked with F(ab')$_2$ goat anti-mouse Ig for 3 min at 37° C. Cells were lysed in TBS containing 1% NP-40 and protease inhibitors. Total cell lysates or immunoprecipitates of DAP12-FLAG with anti-FLAG mAb M2 were analyzed by Western blot using HRP-conjugated anti-phosphotyrosine mAb 4G10 (UBI). Jurkat cells stably transfected with the NKAT5 cDNA (Colonna and Samaridis (1995) *Science* 268:405408) using a retroviral vector (Onihsi, et al. (1996) *Exp. Hematology* 24:324–329) were transiently transfected by electroporation with human DAP12 cDNA in the pEF-BOS vector or sham-transfected with a control vector. Wu, et al. (1995) *Mol. Cell. Biol.* 15:4337–4346. After 24 hours, transfectants were incubated in microtiter plates pre-coated (5 µg/ml) with control Ig or anti-KIR mAb DX27. After 12 hr incubation, transfectants were harvested and then stained with FITC conjugated anti-CD69 or control mAb and analyzed by flow cytometry. Lanier and Recktenwald (1991) *Methods: A Companion to Methods in Enzymology* 2:192–199.

XII. DAP12 Associates with Activating CD94/NKG2C NK Cell Receptors

While the inhibitory NK cell receptors for MHC class I express Immunoreceptor Tyrosine-based Inhibitory Motifs (ITIM) that recruit intracellular tyrosine phosphatases and prevent NK cell effector function, the activating NK cell receptors lack intrinsic sequences required for cellular stimulation. CD94/NKG2C, an activating NK cell receptor of the C-type lectin superfamily which binds to HLA-E, non-covalently associates with DAP12, a membrane receptor containing an Immunoreceptor Tyrosine-based Activating Motif (ITAM). Efficient expression of CD94/NKG2C on the cell surface requires the presence of DAP12 and charged residues in the transmembrane domains of DAP12 and NKG2C are necessary for this interaction. These results provide a molecular basis for the assembly of NK cell receptors for MHC class I involved in cellular activation and inhibition.

NK cells are lymphocytes that participate in innate immune responses against certain bacteria, parasites, and viruses (reviewed in Scott and Trinchieri (1995) *Current Opinion Immunol.* 7:34–40; Trinchieri (1989) *Adv. Immunol.* 47:187–376). How NK cells recognize pathogens is unclear; however, one aspect of this process may involve the detection and elimination of host cells that have lost or down-regulated expression of MHC class I as a consequence of infection. NK cells express receptors for MHC class I that can either activate or inhibit cell-mediated cytotoxicity and cytokine production (reviewed in Lanier, (1998) *Cell* 92:705–707; Lanier (1998) *Ann. Rev. Immunol.* 16:359–393). Several types of NK cell receptors for MHC class I have been identified (Lanier (1998) *Cell*

92:705–707). In humans, the Killer Cell Inhibitory Receptors (KIR) comprise a small family of molecules encoded by genes of the Ig superfamily (Colonna and Samaridis (1995) *Science* 268:405–408; D'Andrea, et al: (1995) *J. Immunol.* 155:2306–2310; Wagtmann, et al. (1995) *Immunity* 2:439–449). Within the KIR family, certain isoforms possess two Ig-domains (KIR2D) or three Ig-domains (KIR3D) in the extracellular region that are involved in recognition of polymorphic HLA-C or HLA-B ligands, respectively (Dohring and Colonna (1996) *Eur. J. Immunol.* 26:365–369; Fan, et al. (1996) *Proc. Nat'l Acad. Sci. USA* 93:7178–7183; Litwin, et al. (1994) *J. Exp. Med.* 180:537–543; Rajagopalan and Long (1997) *J. Exp. Med.* 185:1523–1528; Rojo, et al. (1997) *Eur. J. Immunol.* 27:568–571; and Wagtmann, et al. (1995) *Immunity* 3:801–809). Heterogeneity also exists in the transmembrane and cytoplasmic domains of different KIR molecules. Upon ligand binding, KIR having ITIM in their cytoplasmic domain (designated KIR2DL and KIR3DL) recruit SHP-1 and prevent NK cell effector function (Burshtyn, et al. (1996) *Immunity* 4:77–85; Campbell, et al. (1996) *J. Exp. Med.* 184:93–100; Fry, et al. (1996) *J. Exp. Med.* 184:295–300; and Olcese, et al. (1996) *J. Immunol.* 156:4531–4534). In contrast, KIR isoforms lacking ITIM and having a basic K amino acid in the transmembrane (KIR2DS and KIR3DS) have been implicated in NK cell activation (Biassoni, et al. (1996) *J. Exp. Med.* 183:645–650; Olcese et al. (1997) *J. Immunol.* 158:5083–5086). KYR2DS are non-covalently associated with an ITAM-bearing adapter molecule, DAP12, that is expressed on the surface of NK cells as a disulfide-bonded homodimer (Campbell, et al. (1998) *Eur. J. Immunol.* 28:599–609; Lanier (1998) *Cell* 92:705–707; Olcese, et al. (1997) *J. Immunol.* 158:5083–5086). Upon cross-linking of KIR2DS, tyrosine residues in the ITAM of DAP12 become phosphorylated and recruit ZAP-70 or Syk, resulting in cellular activation (Lanier (1998) *Cell* 92:705–707). Human DAP12 is present on human chromosome 19q13.1 near the KIR gene family (Baker, et al. (1995) *Chromosome Research* 3:511), demonstrating a genetic linkage between KIR and DAP12.

Another type of NK cell receptor, CD94/NKG2, is a heterodimer composed of an invariant CD94 glycoprotein that is disulfide-bonded to either a NKG2A or a NKG2C glycoprotein (Brooks, et al. (1997) *J. Exp. Med.* 185:795–800; Carretero, et al. (1997) *Eur. J. Immunol.* 27:563–575; Lazetic, et al. (1996) *J. Immunol.* 157:4741–4745). CD94 (Chang, et al. (1995) *Eur. J. Immunol.* 25:2433–2437) and four NKG2 genes (NKG2A, NKG2C, NKG2E, and NKG2D/F; Houchins, et al. (1991) *J. Immunol.* 158:3603–3609; and Plougastel and Trowsdale (1997) *Eur. J. Immunol.* 27:2835–2839) are all members of the C-type lectin superfamily and are closely linked on human chromosome 12 p12-p13 in the "NK complex" (Renedo, et al. (1997) *Immunogenetics* 46:307–311). Rodent homologs of the human CD94 and NKG2 genes are located in the "NK complex" on mouse and rat chromosomes syntenic with human chromosome 12 (Berg, et al. (1998) *Eur. J. Immunol.* 28:444–450; Dissen, et al. (1997) *Eur. J. Immunol.* 27:2080–2086; and Vance, et al. (1997) *Eur. J. Immunol.* 27:3236–3241).

Antibodies against CD94 can either activate or inhibit NK cell-mediated cytotoxicity against Fc-receptor bearing targets and different NK cell clones isolated from a single individual demonstrate heterogeneous behavior in these functional assays (Brumbaugh, et al. (1996) *J. Immunol.* 157:2804–2812; Perez-Villar, et al. (1996) *J. Immunol.* 157:5367–5374; and Pérez-Villar et al. (1995) *J. Immunol.* 154:5779–5788). This phenomenon was explained by the finding that CD94 forms disulfide-linked heterodimers with either NKG2A or NKG2C (Brooks, et al. (1997) *J. Exp. Med.* 185:795–800; Cantoni, et al. (1998) *Eur. J. Immunol.* 28:327–338; Carretero, et al. (1997); and Lazetic, et al. (1996) *J. Immunol.* 157:4741–4745). NKG2A contains an ITIM sequence in the cytoplasmic domain that upon receptor ligation becomes tyrosine phosphorylated and recruits SHP-1 or SHP-2 which in turn inhibit NK effector function (Houchins, et al. (1997) *J. Immunol.* 158:3603–3609; and Le Drean, et al. (1998) *Eur. J. Immunol.* 28:264–276). In contrast, NKG2C lacks an ITIM and receptor ligation results in NK cell activation (Cantoni, et al. (1998) *Eur. J. Immunol.* 28:327–338; and Houchins, et al. (1997) *J. Immunol.* 158:3603–3609). CD94 is necessary to transport both NKG2A and NKG2C to the cell surface (Lazetic, et al. (1996) *J. Immunol.* 157:4741–4745). Within the INK cell population in an individual, CD94/NKG2A and CD94/NKG2C receptors are expressed on overlapping subpopulations and some NK cells may express CD94 proteins that are not associated with either NKG2A or NKG2C (Cantoni, et al. (1998) *Eur. J. Immunol.* 28:327–338). Thus, CD94 and the NKG2 proteins can form a diverse receptor repertoire in an individual. CD94/NKG2A and CD94/NKG2C receptors recognize HLA-E (Borrego, et al. (1998) *J. Exp. Med.* 187:813–818; Braud, et al. (1998) *J. Immunol.* 159:5192–5196), a non-classical MHC class I molecule that has the unique property of binding 9 amino acid peptides derived from the leader segments of other classical HLA class I proteins (Braud, et al. (1997) *Eur. J. Immunol.* 27:1164–1169). While the ITIM in NKG2A explains the inhibitory function of the CD94/NKG2A receptor, neither CD94 nor NKG2C possess sequences in their cytoplasmic domains that provide for intrinsic signaling capacity. However, the existence of a basic amino acid in the transmembrane of NKG2C suggested possible interactions with the DAP12 receptor.

Association of DAP12 with CD94/NKG2C Receptors

To determine whether DAP12 might be associated with the activating CD94/NKG2C receptor complex, A mouse pre-B cell line, Ba/F3, was co-infected with ecotropic retroviruses encoding human CD94, NKG2C, and DAP12 (containing a FLAG epitope on the N-terminus to permit detection on the cell surface). Consistent with prior results (Lanier (1998) *Cell* 92:705–707), transfection of FLAG-DAP12 alone into Ba/F3 cells does not permit cell surface expression of this receptor, although FLAG-DAP12 proteins were detected in the cytoplasm of these transfectants as determined by cytoplasmic staining and Western blot analysis. Similarly, cell surface expression of NKG2C alone in Ba/F3 cells or in FLAG-DAP12+ Ba/F3 transfectants co-infected with NKG2C could was not detected. In contrast, CD94 alone was expressed on the cell surface of Ba/F3 cells. However, CD94 is not competent to transport FLAG-DAP12 to the cell surface in Ba/F3 cells co-infected with both CD94 and FLAG-DAP12, although FLAG-DAP12 was detected in the cytoplasm of these transfectants by Western blot and cytoplasmic immunofluorescence. Furthermore, when CD94+ Ba/F3 cells were infected with a retrovirus encoding NKG2C, CD94/NKG2C heterodimers on the cell surface, using an antiserum that detects the CD94/NKG2C complex were not detected (Braud, et al. (1998) *J. Immunol.* 159:5192–5196; Lazetic, et al. (1996) *J. Immunol.* 157:4741–4745) (although it is possible to obtain low levels of surface expression of CD94/NKG2C heterodimers using episomal vectors containing strong promoters in highly efficient transfection systems such as 293T cells; Braud, et al. (1998) *J. Immunol.* 159:5192–5196; Lazetic, et al. (1996) *J. Immunol.* 157:4741–4745). When Ba/F3 cells were infected with retroviruses encoding human CD94, NKG2C, and FLAG-DAP12, expression of FLAG-DAP12 and a CD94/NKG2C receptor on the cell surface of the CD94/NKG2C/DAP12 transfectants were detected. Collectively, these experiments support the existence of a multi-subunit receptor complex composed of CD94, NKG2C, and DAP12.

Ba/F3 transfectants expressing CD94, NKG2C, and FLAG-DAP12 were labeled with $^{125}$I, solubilized in digitonin detergent to preserve non-covalent membrane receptor complexes (Lanier, et al. (1989) *Nature* 342:803–805), and immunoprecipitated with antibodies against human CD94 or FLAG. Immunoprecipitation with anti-CD94 from the CD94/NKG2C/FLAG-DAP12 Ba/F3 transfectants revealed $^{125}$I labeled proteins consistent with the predicted mobility of NKG2C and FLAG-DAP12. It has been previously reported that human CD94 does not label efficiently with $^{125}$I (Lazetic, et al. (1996) *J. Immunol.* 157:4741–4745; Phillips, et al. (1996) *Immunity* 5:163–172), so the –40 kD radiolabeled subunit immunoprecipitated with anti-CD94 mAb represents a NKG2C glycoprotein that is disulfide-bonded to CD94 (Lazetic, et al. (1996) *J. Immunol.* 157:4741–4745). When analyzed using non-reducing conditions, FLAG-DAP12 migrated predominately as a disulfide-bonded homodimer and the mobility of NKG2C was consistent with the existence of a CD94/NKG2C heterodimer. Therefore, it appears that the minimal CD94/NKG2C-DAP12 receptor complex may be a tetramer comprised of a disulfide-linked DAP12 homodimer non-covalently associated with a disulfide-linked CD94/NKG2C heterodimer.

XIII. DAP12 is Required for Cell Surface Expression of CD94/NKG2C Using Charged Residues in the Transmembrane Domains of DAP12 and NKG2C.

The Role of Charged Amino Acids in the Transmembrane of KIR, NKG2, and DAP12 Receptors in the Assembly of the Multi-Subunit Complexes The NKG2A and NKG2C proteins demonstrate 75% amino acid identity (Houchins, et al. (1991) *J. Immunol.* 158:3603–3609) and both CD94/NKG2A and CD94/NKG2C receptors bind to a common ligand, HLA-E (Braud, et al. (1998) *J. Immunol.* 159:5192–5196). A conspicuous difference between NKG2A and NKG2C is the presence of a basic residue in the transmembrane of NKG2C that is absent in NKG2A and CD94. In contrast to NKG2C, infection of CD94+ Ba/F3 cells with a retrovirus encoding human NKG2A permits expression of a CD94/NKG2A complex on the cell surface in the absence of DAP12. The presence of a CD94/NKG2A complex on Ba/F3 cells does not permit expression of FLAG-DAP12 on the cell surface, although FLAG-DAP12 proteins were detected in the cytoplasm of these transfectants by immunofluorescence and Western blot analysis.

Because other multi-subunit membrane receptors have been shown to associate via salt bridges formed by acidic and basic amino acids in their transmembranes (e.g., CD3/TcR (Bonifacino, et al. (1991) *EMBO J.* 10:2783–2793; Cosson, et al. (1991) *Nature* 351:414–416; Morley, et al. (1988) *J. Exp. Med.* 168:1971–1978), the requirement of the D residue in DAP12 was examined for association with CD94/NKG2C. The D residue in FLAG-DAP12 was converted to A by site-directed mutagenesis and this mutant receptor was transfected into Ba/F3 cells. Unlike wild-type FLAG-DAP12, the D-A transmembrane FLAG-DAP12 mutant receptor was expressed on the cell surface in the absence of other subunits, indicating that the D residue in the transmembrane serves as a retention signal for DAP12, similar to the function of the charged residues in the transmembrane of the CD3 proteins (Bonifacino, et al. (1990) *Cell* 63:503–513; Bonifacino, et al. (1991) *EMBO J.* 10:2783–2793; Cosson, et al. (1991) *Nature* 351:414–416). As noted previously, Ba/F3 cells transfected with CD94 and NKG2C do not efficiently express a CD94/NKG2C heterodimer on the cell surface in the absence of DAP12. Infection of these CD94/NKG2C+ Ba/F3 transfectants with the D-A transmembrane FLAG-DAP12 mutant receptor did not permit efficient expression of CD94/NKG2C on the cell surface, as indicated by the marginal reactivity of these cells with an anti-CD94/NKG2 specific antisera (although NKG2C proteins were detected in the cytoplasm of the transfectant by Western blot analysis).

Comparison of the transmembrane domains of NKG2A and NKG2C indicates the presence of a K residue in NKG2C, suggesting this residue may be responsible for interaction with the D residue in DAP12. Therefore, the K in NKG2C was converted to L by site-directed mutagenesis and the K-L transmembrane NKG2C mutant was transfected into Ba/F3 cells expressing DAP12 and CD94. Ba/F3 cells co-transfected with CD94 and the K-L transmembrane NKG2C mutant expressed did not permit surface expression of FLAG-DAP12, although DAP12 was detected in the cytoplasm by Western blot analysis. Very low levels of a CD94/K-L transmembrane NKG2C mutant receptor were detected on the surface of these transfectants using an anti-CD94/NKG2C antiserum. Although the K residue in the transmembrane of NKG2C might serve as a retention signal, it should be noted that NKG2C also expresses the motif DxxxLL that is also present in CD3γ and has been implicated in the degradation, transport and localization of CD3 proteins (Dietrich, et al. (1994) *EMBO J.* 13:2156–2166; Dietrich, et al. (1997) *J. Cell Biol.* 138:271–281; Dietrich, et al. (1996) *J. Cell Biol.* 132:299–310; Letourneur and Klausner (1992) *Cell* 69:1143–1157) and in the binding of Adapter Protein-1 (AP-1) and Adapter Protein-2 (AP-2; Dietrich, et al. (1997) *J. Cell Biol.* 138:271–281).

XIV. Signal Transduction via CD94/NKG2C/DAP12 and KIR2DS2/DAP12 Complexes

Ligation of KIR2DS2 in transfectants expressing KIR2DS2/DAP12 complexes results in the tyrosine phosphorylation of DAP12 and other cellular substrates and the association of phosphorylated DAP12 with Syk (Lanier (1998) *Cell* 92:705–707). Ligation of either CD94 or FLAG-DAP12 on Ba/F3 transfectants expressing CD94/NKG2C/DAP12 complexes caused tyrosine phosphorylation of numerous cellular proteins, including DAP12 and Syk. These results indicate that cross-linking CD94/NKG2C induces cellular activation, presumably via DAP12. It was not addressed whether ligation of CD94/NKG2C in the absence of DAP12 or in transfectants expressing the D-A transmembrane FLAG-DAP12 mutant has functional consequences because CD94/NKG2C was not efficiently expressed in the absence of wild-type DAP12.

Unlike CD94/NKG2C, KIR2DS2 molecules are expressed on the cell surface in the absence of DAP12, although they are unable to induce cellular activation (Bléry, et al. (1997) *J. Biol. Chem.* 272:8989–8996; Lanier, et al. (1998) *Nature* 391:703–707). KIR2DS2+ Ba/F3 cells were infected with retroviruses encoding either wild-type FLAG-DAP12 or the D-A transmembrane FLAG-DAP12 mutant receptor. Both KIR2DS2 and the mutant DAP12 protein were expressed on the cell surface. However, the D-A transmembrane FLAG-DAP12 mutant protein was not co-immunoprecipitated with KIR2DS2 from $^{125}$I labeled transfectants. Furthermore, ligation with anti-KIR mAb failed to activate these cells, whereas direct cross-linking of the D-A transmembrane FLAG-DAP12 mutant receptor with anti-FLAG mAb did induce tyrosine phosphorylation of cellular proteins. Like NKG2A and NKG2C, the KIR2DS2 protein has a counterpart, KIR2D12, that lacks a charged amino acid in the transmembrane and contains an ITIM in its cytoplasmic domain. It has been previously reported that KIR2DL2 is unable to associate with DAP12 (Lanier, et al. (1998) Nature 391:703–707). Collectively, these findings indicate that the association of DAP12 with either KIR2DS2 or CD94/NKG2C complexes likely results from interactions involving the transmembrane domains of these proteins.

The stoichiometry of DAP12 and KIR2DS2 or CD94/NKG2C in these complexes has not been determined. A DAP12 disulfide-linked homodimer possesses two D residues (i.e., one in each DAP12 protein) that could interact with the K residues present in the transmembranes of KIR2DS2 or NKG2C. Because CD94 lacks charged residues in the transmembrane, DAP12 may be able to function as an adapter permitting the association of two KIR2DS2 monomers or two CD94/NKG2C heterodimers with a single DAP12 homodimer.

XV. Association of DAP12 and CD94 in Human NK cells

CD94/NKG2C receptors previously have been implicated in NK cell activation (Cantoni, et al. (1998) Eur. J. Immunol. 28:327–338; Houchins, et al. (1997) J. Immunol. 158:3603–3609). A NK cell clone and a polyclonal NK cell line were selected based on their ability to mediate re-directed cytotoxicity against the Fc receptor-bearing P815 target cell in the presence of anti-CD94 mAb, suggesting the presence of an activating CD94-associated receptor complex, probably CD94/NKG2C (Cantoni, et al. (1998) Eur. J. Immunol. 28:327–338). The NK cell clone and the polyclonal NK cell line were $^{125}$I labeled, lysed in digitonin detergent to preserve multi-subunit receptor complexes, and DAP12-associated proteins were co-immunoprecipitated using an anti-DAP12 antiserum. DAP12-associated proteins were eluted with a pH 11.5 buffer to dissociate the complexes and then the eluted proteins were re-immunoprecipitated with a control mAb or anti-CD94 mAb. For the polyclonal NK cell line, anti-CD94 mAb specifically reacted with an $^{125}$I protein eluted from the initial anti-DAP12 immunoprecipitate. On SDS-PAGE analysis, this molecule migrated at ~70 kD in non-reducing conditions and ~40 kD in reducing conditions. Equivalent results were obtained using the NK cell clone. Because CD94 itself does not $^{125}$I label (Lazetic, et al. (1996) J. Immunol. 157:4741–4745; Phillips, et al. (1996) Immunity 5:163–172), it seems likely that the CD94-associated $^{125}$I labeled protein represents NKG2C, although NKG2C-specific serological reagents are not available to confirm this. Nonetheless, these finding demonstrate the existence of a CD94/DAP12 receptor complex on the cell surface of human NK cells.

Paired Activating and Inhibitory Receptors

The KIR gene family encodes receptors that have been implicated in either cellular activation or inhibition (Biassoni, et al. (1996) J. Exp. Med. 183:645–650; Olcese, et al. (1997) J. Immunol. 158:5083–5086). The inhibitory receptors contain ITIM sequences in their cytoplasmic domains and lack charged residues in the transmembrane segments, whereas the activating receptors lack ITIM, often have shorter cytoplasmic regions, and possess a charged amino acid in the transmembrane. This general strategy is also evident in the NKG2 (Houchins, et al. (1991) J. Immunol. 158:3603–3609), Ly49 (Smith, et al. (1994) J. Immunol. 153:1068–1079), PIR (Hayami, et al. (1997) J. Biol. Chem. 272:7320–7327; Kubagawa, et al. (1997) Proc. Nat'l Acad. Sci. USA 94:5261–5266) and ILT (LIR) (Borges, et al. (1997) J. Immunol. 159:5192–5196; Samaridis and Colonna (1997) Eur. J. Immunol. 27:660–665) gene families, which all include potentially inhibitory and activating receptors.

It has been shown herein, that DAP12 associates with the activating isoforms of both the KIR and CD94/NKG2 receptors. The inhibitory CD94/NKG2A and activating CD94/NKG2C receptors both bind the same ligand, HLA-E (Braud, et al. (1998) J. Immunol. 159:5192–5196). What is the biological rationale for paired inhibitory and activating receptors recognizing MHC class I? The activating CD94/NKG2C/DAP12 receptor complex may function to stimulate tyrosine kinases that phosphorylate the ITIM sequences in the inhibitory NKG2A receptor, resulting in the recruitment of SHP-1 or SHP-2 (Le Drean, et al. (1998) Eur. J. Immunol. 28:264–276). However, this seems unlikely since NKG2A and NKG2C are differentially expressed within the total NK cell population and only a subset of NK cells expresses both receptors (Cantoni, et al. (1998) Eur. J. Immunol. 28:327–338; and Houchins, et al. (1997) J. Immunol. 158:3603–3609). The existence of NK cells expressing CD94/NKG2C, in the absence of the inhibitory CD94/NKG2A receptor, provides the potential for activation of these cells upon encountering HLA-E. HLA-E is broadly expressed in normal tissues (Geraghty, et al. (1992) Proc. Natl. Acad. Sci. USA 89:2669–2673; Lee, et al. (1998) Proc. Natl. Acad. Sci. USA 95:5199–5204; Ulbrecht, et al. (1992) J. Immunol. 149:2945–2953); therefore, activation of NK cells via CD94/NKG2C/DAP12 might result in autoimmunity. However, recent studies suggest that all NK cell clones appear to express at least one inhibitory receptor (either a KIR or CD94/NKG2A) against a self MHC class I ligand, thus preventing destruction of normal autologous tissues (Uhrberg, et al. (1997) Immunity 7:753–763; Valiante, et al. (1997) Immunity 7:739–751). NK cell clones expressing activating CD94/NKG2C/DAP12 receptors and an inhibitory KIR against a self class I ligand could potentially recognize and eliminate host cells that have lost expression of the KIR class I ligand, but retained expression of HLA-E. This model requires experimental testing, but would provide defense against pathogens that encode leader peptides competent to bind HLA-E, but down-regulate expression of conventional MHC class I molecules as a consequence of infection.

Transfectants cDNA used were human CD94 (Chang, et al., 1995), NKG2A and NKG2C (Houchins, et al. (1991) J. Immunol. 158:3603–3609), KIR2DS2 (NKAT5, (Colonna and Samaridis, 1995)) and FLAG-DAP12 (Lanier, et al. (1998) Nature 391:703–707). The D-A transmembrane FLAG-DAP12 mutant cDNA with an A residue (codon GCC) substituted for the D residue (codon GAC) and the K-L transmembrane NKG2C mutant cDNA with a L residue (TTA) substituted for K (codon AAA) were generated by PCR mutagenesis using conventional techniques. A NKG2C cDNA containing a FLAG epitope on the COOH terminus immediately prior to the NKG2C stop codon was generated by PCR. cDNA were sequenced and subcloned into the pMX-neo or pMX-puro retroviral vectors (Onihsi, et al. (1996) Exp. Hematology 24:324–329). Plasmid DNA was transfected into Φ-NX-E ecotropic retrovirus packaging cells (a generous gift from G. Nolan (Stanford University))

using lipofectamine (Gibco-BRL) (Onihsi, et al., 1996). Viral supernatants were collected two days later and used to infect mouse Ba/F3 pre-B cells (Onihsi, et al., 1996). Two days post-infection cells were switched to selection medium and Ba/F3 cells stably expressing human NK cell receptors were sorted by flow cytometry for homogeneous high level expression.

Antibodies and Flow Cytometry mAbs used were anti-CD94 (DX22; Phillips, et al. (1996) *Immunity* 5:163–172) or HP-3D9 mAb (Lopez-Botet (1995), pp. 1437–1439, in Schlossman, et al. (eds.) Leucocyte Typing V. Oxford University Press, Oxford; anti-KIR2D mAb (DX27; Phillips, et al. (1996) *Immunity* 5:163–172), anti-NKR-P1A (DX1; Lanier et al. (1994) *J. Immunol.* 153:2417–2428), anti-FLAG (M2 mAb, Kodak), anti-NKG2A/C (8E4 mAb; Houchins, et al. (1997) *J. Immunol.* 158:3603–3609) and control mouse IgG1 mAb (Becton Dickinson, San Jose, Calif.). Rabbit antiserum specific for the CD94/NKG2A and CD94/NKG2C heterodimers was prepared as described (Lazetic, et al. (1996) *J. Immunol.* 157:4741–4745). FITC conjugated goat anti-rabbit Ig and FITC conjugated anti-mouse Ig second antibodies were purchased from CalTag (So. San Francisco, Calif.). Immunofluorescence and flow cytometry were performed as described (Lanier and Recktenwald (1991) *Methods: A Companion to Methods in Enzymology* 2:192–199).

Biochemistry

Transfected Ba/F3 cells were labeled with $^{125}$I and solubilized in digitonin lysis buffer (pH 7.8, 1% digitonin, 0.12% Triton-X100, 150 mM NaCl, 20 mM triethanolamine, 0.01% NaN$_3$, and protease inhibitors; Lanier, et al. (1989) *Nature* 342:803–805). Cell lysates were incubated on ice for 2 hr with Pansorbin (Calbiochem) coated with rabbit anti-mouse/rat Ig (Sigma) and anti-CD94 (DX22 mAb), anti-FLAG (M2 mAb) or control IgG and then washed. Immunoprecipitates were resuspended in SDS-PAGE sample buffer in the presence or absence of 10% 2-mercaptoethanol, run on 18% Tris/glycine gels (Novex) and visualized by using a PhosphorImager (Molecular Dynamics).

A human NK cell clone and a polyclonal human NK cell line (CD3−, CD56+ peripheral blood NK cells cultured as described (Yssel, et at. (1984) *J. Exp. Med.* 160:239–254) were labeled with $^{125}$I and solubilized in digitonin lysis buffer. $^{125}$I cell lysates were pre-cleared overnight with Pansorbin coated with rabbit Ig and then incubated on ice for 2 hr with Pansorbin coated with an affinity purified rabbit anti-DAP12 antiserum (generated by standard methods against a GST fusion protein containing the entire cytoplasmic domain of human DAP12). DAP12-associated proteins were eluted in 25 μl 50 mM diethylamine (pH 11.5) and transferred to 0.5 ml 1% NP-40 lysis buffer (50 mM Tris, 150 mM NaCl, pH 8.0 containing protease inhibitors) with 10 mg/ml BSA carrier protein. The DAP12-associated eluted proteins were re-immunoprecipitated anti-CD94 mAb (HP-3D9 and DX22) coupled Sepharose beads or anti-NKR-PIA mAb (DX1) coupled Sepharose beads (used as a negative control). Immunoprecipitates were washed in 1% NP-40 lysis buffer, resuspended in SDS-PAGE sample buffer in the presence or absence of 10% 2-mercaptoethanol, run on 18% Tris/glycine gels and visualized by using a PhosphorImager.

Western blot analysis using anti-FLAG (M2 mAb) or anti-NKG2A/C (8E4 mAb; Houchins, et al. (1997) *J. Immunol.* 158:3603–3609) was performed as described in Phillips, et al. (1996) *Immunity* 5:163–172. 8E4 mAb detects both NKG2A and NKG2C by Western blot analysis, but does not immunoprecipitate or bind to these antigens in immunofluorescence assays.

Cellular Stimulation

Transfected Ba/F3 cells were suspended in cold PBS with 0.5% BSA at 5×10$^7$ cells/ml containing 20 μg/ml mAb recognizing CD94, FLAG-DAP12, or KIR2DS2. Cells were incubated on ice for 30 minutes, washed, resuspended in 10 μg/ml goat anti-mouse IgG F(ab')$_2$ (Jackson Immunoresearch), and incubated for three minutes at 37° C. Cells were pelleted, resuspended at 10$^8$/ml in ice cold lysis buffer (1% NP-40, 10 mM Tris, pH 7.4, 150 mM NaCl containing the protease and phosphates inhibitors-aprotinin, leupeptin, PMSF, EDTA, NaVO$_4$, and NaF) as described (Lanier, et al. (1998) *Nature* 391:703–707). Syk and FLAG-DAP12 were immunoprecipitated with rabbit anti-Syk antiserum (generously provided by Joe Bolen, DNAX) or anti-FLAG (M2 mAb). Cell lysates (2–3×10 cell equivalents) and immunoprecipitates were run on Tris/glycine gels, blotted onto Immobilon membranes (Millipore), blocked, probed with horseradish peroxidase-conjugated anti-phosphotyrosine mAb 4G10 (Upstate Biotechnology), washed, and developed with a chemiluminescent substrate (Pierce).

XVI. Murine DAP12 Associates With Ly49D or Ly49H

Several members of the Ly49 receptor family inhibit NK cell-mediated lysis of targets expressing appropriate MHC class I molecules. Ly49D and Ly49H, two Ly49 molecules that lack Immunoreceptor Tyrosine-based Inhibitory Motifs (ITIM) in their cytoplasmic domains, associate with mouse DAP12, a molecule which possesses an Immunoreceptor Tyrosine-based Activation Motif (ITIM). Co-transfection of either Ly49D or Ly49H with DAP12 induces surface expression of both Ly49 and DAP12. The Ly49/DAP12 complex was co-immunoprecipitated from the transfected cells, demonstrating a physical association of DAP12 with Ly49D or Ly49H in the plasma membrane. Stimulation of transfectants with antibodies recognizing either Ly49D or Ly49H results in cellular activation as assessed by induction of tyrosine phosphorylation of multiple cellular substrates.

NK cells express receptors for MHC class I which upon recognition of appropriate polymorphic class I ligands deliver an inhibitory signal, resulting in the inhibition of target lysis. Mouse Ly49A, the prototypic inhibitory receptor for H-2 (Karlhofer, et al. (1992) *Nature* 358:66), is a homodimeric type II integral membrane protein of the C-type lectin family expressed on natural killer cells and a small population of T cells. The Ly49 family includes 9 genes, Ly49A through I (Smith, et al. (1994) *J. Immunol.* 153:1068; Brennan, et al. (1994) *J. Exp. Med.* 180:2287; Takei, et al. (1997) *Immunol. Rev.* 155:67). Seven of the Ly49 molecules (Ryan and Seaman (1997) *Immunol Rev.* 155:79) possess an ITIM (V/IxYxxL/V) (Thomas (1995) *J. Exp. Med.* 181:1953; Lanier (1997) *Immunity* 6:371) in their cytoplasmic domains. The phosphorylated ITIM in Ly49A and Ly49G2 bind the cytoplasmic tyrosine phosphatases SHP-1 and SHP-2 (Olcese, et al. (1996) *J. Immunol.* 156:4531; Nakamura, et al. (1997) *J. Exp. Med.* 185:673; and Mason, et al. (1997) *J. Immunol.* 159:4187). Engagement of Ly49A by its ligand H-2D$^d$ interrupts early activation events induced by interaction of NK cells with target cells (Nakamura, et al. (1997) *J. Exp. Med.* 185:673). Ly49D and Ly49H, lack ITIM and possess a positively charged arginine residue within their transmembrane domains. Ly49D is unable to deliver an inhibitory signal and in fact may activate NK cells (Mason, et al. (1996) *J. Exp. Med.* 184:2119).

Human NK cells express a functionally analogous set of molecules, the killer cell inhibitory receptors (KIR), which belong to the immunoglobulin superfamily (Lanier (1997)

*Immunity* 6:371). KIR, like Ly49, can be divided into two sub-families based on the presence or absence of ITIM in their cytoplasmic domains. KIR2DL or KIR3DL possess ITIM and inhibit lysis of targets expressing their MHC class I ligands. KIR isoforms lacking ITIM (KIR2DS) possess a positively charged residue in their transmembrane domains and deliver an activating signal (Moretta, et al. (1995) *J. Exp. Med.* 182:875; Biassoni, et al. (1996) *J. Exp. Med.* 183:645). DAP12, which non-covalently associates with KIR2DS2 (Lanier, et al. (1998) *Nature* 391:703–707), possesses an ITAM in its cytoplasmic tail and a negatively charged aspartic acid residue in its transmembrane domain. Ligation of the KIR2DS2/DAP12 complex results in cellular activation. The association of mouse DAP12 with Ly49D and Ly49H, and the ability of these complexes to activate downstream signaling pathways was examined.

Transcripts of Ly49D and Ly49H are present in IL-2 activated NK cells (20). Ly49D is expressed on 50% of NK cells (Mason, et al. (1996) *J. Exp. Med.* 184:2119), and is associated with a tyrosine phosphoprotein of 16 kD (Mason, et al. (1998) *J. Immunol.* 160:4148–4152). Murine NK cells, like human NK cells, transcribe mRNA for DAP12, a molecule which associates with the activating KIR2DS and mediates cellular activation (Lanier, et al. (1998) *Nature* 391:703). To examine if Ly49D or Ly49H associated with DAP12, Ba/F3 cells were stably transfected with an epitope-tagged mouse DAP12 (DAP12-FLAG). Ba/F3-DAP12-FLAG cells do not express DAP12 on the cell surface. Ba/F3 or the Ba/F3-DAP12 transfectants were then infected with retroviruses encoding either Ly49D, a myc epitope tagged Ly49H (Ly49H-myc), or as a control Ly49A. Neither Ly49D nor Ly49H-myc was expressed at appreciable levels on the cell surface when transfected into Ba/F3 cells. In contrast, transfection of Ba/F3-DAP12-FLAG cells with either Ly49D or Ly49H-myc resulted in high level surface expression of both Ly49 and DAP12-FLAG, suggesting that Ly49D and Ly49H associate with DAP12.

It was examined whether the charged residues in the transmembranes of Ly49 and DAP12 are important for their association. Ly49A shares 86% amino acid identity with Ly49D in its extracellular domain, but lacks the arginine in its transmembrane segment. In contrast to Ly49D or Ly49H, when Ly49A was stably transfected into Ba/F3 or Ba/F3-DAP12-FLAG cells, it was expressed at the cell surface alone or in the presence of DAP12-FLAG and failed to induce surface expression of DAP12-FLAG. Interactions between Ly49D or Ly49H-myc and DAP12 are not species-restricted because both Ly49 molecules were expressed on the surface of Ba/F3-human DAP12-FLAG transfectants. However, neither Ly49D or Ly49H were expressed on the surface of Ba/F3 cells stably transfected with a mutant human DAP12 molecule in which the negatively charged aspartic acid in the transmembrane was mutated to leucine. Therefore, both Ly49D and Ly49H must associate with DAP12 to effectively reach the cell surface and their interaction is likely mediated by the oppositely charged residues in the transmembranes of DAP12 and Ly49.

To confirm that Ly49D and Ly49H non-covalently associate with DAP12 at the cell surface, Ly49D/DAP12-FLAG or Ly49H-myc/DAP12-FLAG Ba/F3 transfectants were surface iodinated, lysed with digitonin, and immunoprecipitates were analyzed by SDS-PAGE. Immunoprecipitation of Ba/F3-Ly49D/DAP12-FLAG lysates with anti-Ly49D showed two iodinated species with sizes consistent with their identity as Ly49D and DAP12-FLAG. An identical pattern was observed with anti-FLAG, confirming that the two species are Ly49D and DAP12-FLAG. Immunoprecipitation of Ba/F3-Ly49H-myc/DAP12-FLAG lysates with anti-myc or anti-FLAG showed a similar pattern. These results demonstrate a physical interaction of Ly49D or Ly49H with DAP12 in the plasma membrane.

XVII. Ly49/DAP12 Complexes Transmit Intracellular Activating Signals

Since DAP12 possesses an ITAM and engagement of Ly49D activates NK cells (Mason, et al. (1996) *J. Exp. Med.* 184:2119), it was asked if the Ly49/DAP12 complexes transmit an activating signal. Crosslinking of Ly49D/DAP12-FLAG and Ly49H-myc/DAP 12-FLAG transfectants with anti-Ly49 or anti-FLAG resulted in tyrosine phosphorylation of many cellular proteins including DAP12-FLAG and Syk in both cell lines. These data provide evidence that Ly49D/DAP12 and Ly49H/DAP12 form functional complexes at the cell surface which upon ligation can initiate cellular activation.

What are the physiological ligands for these activating receptors? Ly49D shares 86% amino acid identity in its extracellular domain with Ly49A (Smith, et al. (1994) *J. Immunol.* 153:1068), an inhibitory receptor that binds H-2$D^d$ and H-2$D^k$ (Brennan, et al. (1996) *J. Exp. Med.* 183:1553; Kane (1994) *J. Exp. Med.* 179:1011; Daniels, et al. (1994) *J. Exp. Med.* 180:687). Ly491-1 shares 90% amino acid identity in its extracellular domain with another inhibitory receptor Ly49C (Brennan, et al. (1994) *J. Exp. Med.* 180:2287), which interacts with several class I molecules, including H-2 $K^b$ (Brennan, et al. (1996) *J. Exp. Med.* 183:1553). Thus, these activating forms of Ly49 may interact with MHC class I molecules. Evidence for positive allorecognition by NK cells both in vivo and in vitro exists in the rat (reviewed in Rolstad, et al. (1997) *Immunol. Rev.* 155:91). Similarly, mouse NK cells recognize allogeneic bone marrow cells expressing certain class I molecules in a positive fashion and mediate their rejection in vivo (Ohlen, et al. (1989) *Science* 246:666; George, et al. (1997) *Immunol Rev.* 155:29). It has been shown that mouse Ly49D and Ly49H associate with DAP12 and form activating receptors, providing a possible explanation for positive allorecognition by NK cells.

How can the existence of both activating and inhibitory NK receptors which recognize class I ligands be reconciled? Three models are envisioned. In the first model, engagement of activating receptors would function during development to promote maturation of immature NK cells. However, so far there is no evidence for the appearance of activating receptors prior to inhibitory receptors during development. A second model proposes that an NK cell possesses activating and inhibitory receptors for the same class I ligand. Upon engaging class I, the activating receptor would recruit a protein tyrosine kinase that phosphorylates the ITIM of the inhibitory receptor, resulting in NK cell inactivation. While most human NK cell clones possess at least one activating and one inhibitory receptor they do not necessarily possess a pair capable of recognizing the same ligand. Finally, a third model predicts that NK cells express inhibitory and activating receptor for different class I alleles. In this model, engagement of the inhibitory receptor dominates if ligands for both receptors are engaged. If the ligand for the inhibitory receptor is down-regulated or lost, the activating receptor could trigger lysis of the "abnormal" cell if its ligand is present. This model has the advantage that multiple inhibitory and activating receptors could be expressed by the same cell, a prediction more in line with the findings in NK clones. Yet, in the case of loss of all MHC class I molecules by a target cell, other activating mechanisms would have to initiate lysis by the NK cell.

XVIII. Isolation of Associated Proteins

DAP12 remains localized intracellularly when expressed in cells in the absence of associating partners. This observation was exploited with the purpose of cloning novel DAP12-associating proteins, e.g., to expression clone genes necessary in the process of cellular localization to the membrane. Cells lacking the associated proteins were transfected with the DAP12, and the protein remained intracellularly localized. These cells could be used to expression clone necessary accessory proteins for DAP12 surface localization. The strategy had been labeled "DAP-trap".

To this end, a FLAG-tagged form of mouse DAP12 was expressed in 293 T cells using an expression vector, e.g., pREP10. In the presence of hygromycin, a stable DAP12 expressing cell line was selected, DT381. To reduce the background of spontaneous DAP12 expression at the cell surface, DT381 cells were negatively selected by flow cytometry using the M2 anti-FLAG mAb (Kodak). To clone novel DAP12 associating proteins, a J774 macrophage cell line derived pJEF14 expression library was transfected into DT381 cells. Forty-eight hours after transfection, the cells were selected for cell surface expression of DAP12 by flow cytometry. This was performed by two color staining: DAP12 was visualized using the M2 anti-FLAG mAb, followed by a biotin-conjugated anti-mouse IgG1 mAb (#02232D Pharmingen), followed by a streptavidin-PE third step incubation. Fc receptors on transfected DT381 cells were visualized using the directly FITC-conjugated anti-CD16/32 mAb 2.4G2 (#01244D Pharmingen). Only single PE positive cells were sorted. Staining with the anti-CD16/32 mAb was necessary to avoid the cloning of Fc receptors which are abundantly present in J774 cells.

The plasmids from the sorted cells were rescued and the DNA was retransformed into DH10B bacteria. Sublibraries were obtained and subjected to a novel round of expression cloning. After three rounds of selection, 500 single bacterial colonies from the third sublibrary were grown in a 96 well plate format to construct a three dimensional matrix of consisting of 5×12×8 colonies. DNA obtained from pools of each X, Y, and Z coordinate of this matrix was again transfected into DT381 cells and the transfectants were screened for DAP12 surface expression.

This resulted in the identification of two identical clones, both encoding a 165 amino acid type II transmembrane protein of the C-type lectin superfamily. This gene/protein was designated Myeloid DAP12 associating Lectin-1 (MDL-1). This embodiment of MDL-1 from the mouse has an intracellular region of 2 residues, a transmembrane region of 23 residues, and a 140 residue extracellular region containing the C-type lectin domain. The transmembrane segment possesses a charged amino acid, the extracellular region has three putative N-glycosylation sites. BLAST searching revealed a highly homologous full length mouse EST, AA186015, which was identical to the two above mentioned clones, with the exception that this clone has an extra stretch of 75 nucleotides resulting in a 25 residue additional stretch extracellularly just outside of the transmembrane region. Thus, there exist two embodiments, a short form and long form. The rest of the sequences are identical.

Searching within a DNAX sequence database revealed a homologous human EST, #97-1128A12, which encodes a human homologue of MDL-1. The mouse MDL-I appears to be encoded by a single gene, in contrast to many related surface proteins, which may occur in families of genes. The mouse MDL-I expression is restricted to monocytes, macrophages and dendritic cells.

Because the MDL-1 gene appears to be crucial in localization of the DAP12 to the membrane, and possesses interesting structural features, it is likely that the MDL-1 associates with the DAP12 in a membrane complex. Thus, disruption of the complex may lead ton interesting blocking of function of the DAP12-receptor complex. This suggests obvious approaches to small molecule drug screening for compounds which would interfere with association. Alternatively, transmembrane fragments may block functional association. Antibodies to the extracellular regions, either of proteins alone, or the combination of components in the functional complexes, would be useful in diagnostic or therapeutic contexts.

DAP10 also seems to associate with an accessory protein. In particular, immunoprecipitation of DAP10 under mildly denaturing conditions results in co-immunoprecipitation of a protein band of about 40–41 kD. Neuramimidase treatment, or O-glycanase treatment, result in a decrease in molecular weight to about 38–39 kD. N-glycanase treatment causes a decrease in molecular weight to about 28–30 kD. These suggest that the protein is about 26–30 kD without glycosylation. Standard or microsequencing methods can be applied to protein isolated by immunoprecipitation. With sequence, redundant PCR primers, or other techniques can be applied to isolate the gene. Alternatively, sequence may allow identification of the gene by matches in sequence databases.

Moreover, the DAP10 is also subject to the DAP-trap strategy. Expression cloning techniques can be applied, as with the DAP12, to clone the gene from a cDNA library. Distribution information will allow selection of the appropriate cell lines and cDNA libraries for such.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled.

What is claimed is:

1. A binding compound comprising an antigen binding fragment from an antibody, which specifically binds to SEQ ID NOs: 12 or 14.

2. The binding compound of claim 1, wherein the binding compound is:
   a) a polyclonal antibody;
   b) a monoclonal antibody;
   c) a humanized antibody or binding fragment thereof;
   d) an Fab, Fv, or F(ab')$_2$ fragment;
   e) a single chain antibody;
   f) binds to SEQ ID NOs:12 or 14 with a Kd with an affinity that is at least 30 micromolar; or
   g) detectably labeled.

3. The binding compound of claim 1, further comprising a carrier.

4. A kit comprising the binding compound of claim 1 in one or more compartments, and optionally, instructions for use and disposal.

* * * * *